United States Patent
Schuele et al.

(10) Patent No.: US 11,406,536 B2
(45) Date of Patent: Aug. 9, 2022

(54) CONFOCAL DETECTION TO MINIMIZE CAPSULOTOMY OVERCUT WHILE DYNAMICALLY RUNNING ON THE CAPSULAR SURFACE

(71) Applicant: AMO DEVELOPMENT, LLC, Santa Ana, CA (US)

(72) Inventors: Georg Schuele, Portolla Valley, CA (US); Raymond Woo, Los Altos, CA (US); John S. Hart, San Carlos, CA (US)

(73) Assignee: AMO Development, LLC, Santa Ana, CA (US)

( * ) Notice: Subject to any disclaimer, the term of this patent is extended or adjusted under 35 U.S.C. 154(b) by 191 days.

(21) Appl. No.: 16/522,404

(22) Filed: Jul. 25, 2019

(65) Prior Publication Data

US 2019/0343684 A1 Nov. 14, 2019

Related U.S. Application Data

(62) Division of application No. 14/611,661, filed on Feb. 2, 2015, now Pat. No. 10,363,173.
(Continued)

(51) Int. Cl.
*A61F 9/008* (2006.01)

(52) U.S. Cl.
CPC .. *A61F 9/00834* (2013.01); *A61F 2009/0087* (2013.01); *A61F 2009/00872* (2013.01);
(Continued)

(58) Field of Classification Search
CPC .......... A61F 9/00834; A61F 2009/0087; A61F 2009/00872; A61F 2009/00878;
(Continued)

(56) References Cited

U.S. PATENT DOCUMENTS

| | | |
|---|---|---|
| 5,720,894 A | 2/1998 | Neev et al. |
| 5,957,915 A | 9/1999 | Trost |

(Continued)

FOREIGN PATENT DOCUMENTS

| | | | |
|---|---|---|---|
| DE | 102011109058 | * | 1/2013 |
| JP | 2006239092 A | | 9/2006 |

(Continued)

OTHER PUBLICATIONS

International Search Report and Written Opinion for Application No. PCT/US2015/014086, dated Apr. 21, 2015, 12 pages.

*Primary Examiner* — Nathan J Jenness
*Assistant Examiner* — James Moss
(74) *Attorney, Agent, or Firm* — Johnson & Johnson Surgical Vision, Inc.

(57) ABSTRACT

Embodiments of this disclosure disclose an imaging system, including an eye interface device, a scanning assembly, a beam source, a free-floating mechanism, and a detection assembly. The beam source generates an electromagnetic radiation beam. The detection assembly generates a signal indicative of an intensity of a portion of the electromagnetic radiation beam reflected from the focal point location. A subsequent focal point of the electromagnetic radiation beam may be adjusted per the measured intensity signal. In some embodiments, an intensity signal below a lower threshold value may suggest a depth increase for a subsequent focal point. An intensity signal above an upper threshold value may suggest a depth decrease for a subsequent focal point. And, an intensity signal between the lower and upper thresholds may suggest a depth be maintained for a subsequent focal point. The focal point may be adjusted after each pulse or after a plurality of pulses.

20 Claims, 14 Drawing Sheets

Related U.S. Application Data

(60) Provisional application No. 61/950,416, filed on Mar. 10, 2014, provisional application No. 61/935,478, filed on Feb. 4, 2014.

(52) U.S. Cl.
CPC ............... *A61F 2009/00878* (2013.01); *A61F 2009/00887* (2013.01); *A61F 2009/00889* (2013.01); *A61F 2009/00897* (2013.01)

(58) Field of Classification Search
CPC .. A61F 2009/00887; A61F 2009/00889; A61F 2009/00897
See application file for complete search history.

(56) References Cited

U.S. PATENT DOCUMENTS

| | | |
|---|---|---|
| 5,984,916 A | 11/1999 | Lai |
| 6,019,472 A | 2/2000 | Koester et al. |
| 6,454,761 B1 | 9/2002 | Freedman |
| 7,655,002 B2 | 2/2010 | Myers et al. |
| 7,717,907 B2 | 5/2010 | Ruiz et al. |
| 8,262,646 B2 | 9/2012 | Frey et al. |
| 8,350,183 B2 | 1/2013 | Vogel et al. |
| 8,382,745 B2 | 2/2013 | Naranjo-Tackman et al. |
| 8,414,564 B2 | 4/2013 | Goldshleger et al. |
| 8,518,026 B2 * | 8/2013 | Culbertson ........... A61F 2/1648 606/2 |
| 2010/0130966 A1 * | 5/2010 | Brownell ............. A61B 3/1005 606/4 |
| 2011/0022036 A1 | 1/2011 | Frey et al. |
| 2011/0172649 A1 * | 7/2011 | Schuele ............. A61F 9/00827 606/4 |
| 2011/0184395 A1 * | 7/2011 | Schuele ................. A61F 9/008 606/5 |
| 2011/0196350 A1 * | 8/2011 | Friedman ............... A61F 9/008 606/6 |
| 2011/0264081 A1 * | 10/2011 | Reich ................. A61F 9/00838 606/4 |
| 2011/0319873 A1 | 12/2011 | Raksi et al. |
| 2011/0319875 A1 | 12/2011 | Loesel et al. |
| 2013/0274725 A1 * | 10/2013 | Rathjen ............. A61F 9/00806 606/5 |
| 2014/0128821 A1 | 5/2014 | Gooding et al. |
| 2014/0194860 A1 * | 7/2014 | Dick ................... A61F 9/00825 606/6 |
| 2014/0316389 A1 * | 10/2014 | Schuele ............. A61F 9/00825 606/5 |

FOREIGN PATENT DOCUMENTS

| | | | |
|---|---|---|---|
| JP | 2013158599 A | 8/2013 | |
| WO | WO-2009146906 A2 * | 12/2009 | ........... A61B 3/1173 |
| WO | 2012135073 A2 | 10/2012 | |

* cited by examiner using the second support assembly to support a second reflector configured to reflect the electromagnetic radiation beam to propagate along a portion of the variable optical path so as to be incident on the first reflector - 222 using the sensor to generate the intensity signal comprises passing a reflected portion of the electromagnetic radiation beam through an aperture to block portions of the electromagnetic radiation beam reflected from locations other than the focal point location - 224

*FIG. 5* passing the electromagnetic radiation beam through a polarization-sensitive device - 226 modifying polarization of at least one of the electromagnetic radiation beam and a portion of the electromagnetic radiation beam reflected from the focal point location - 228 using the polarization-sensitive device to reflect a portion of the electromagnetic radiation beam reflected from the focal point location so as to be incident upon the sensor - 230

*FIG. 6*

CONFOCAL DETECTION TO MINIMIZE CAPSULOTOMY OVERCUT WHILE DYNAMICALLY RUNNING ON THE CAPSULAR SURFACE

CROSS-REFERENCES TO RELATED APPLICATIONS

This application claims priority to and is a divisional of U.S. patent application Ser. No. 14/11,661, filed on Frb. 2, 2015, which claims priority to U.S. provisional No. 61/935, 478, filed on Feb. 4, 2014, and U.S. provisional No. 61/950, 416, filed on Mar. 10, 2014, the entire contents of each of which are incorporated herein by reference.

BACKGROUND

Over the years, laser eye surgery systems have replaced manual surgical tools in ophthalmic procedures. Indeed, with applications in a variety of different procedures, laser surgery systems have become ubiquitous in ophthalmic surgery.

For example, in the well-known procedure known as LASIK (laser-assisted in situ keratomileusis), a laser eye surgery system employing ultraviolet radiation is used for ablating and reshaping the anterior surface of the cornea to correct a refractive condition, such as myopia or hyperopia. Further, prior to ablation during LASIK, the cornea is incised with a laser eye surgery system employing a non-ultraviolet, ultra-short pulsed laser beam to create a flap to expose an underlying portion of the cornea so that it can be then be ablated and reshaped with ultraviolet laser beams. Afterwards, the treated portion is covered with the flap.

More recently, laser eye surgery systems have been developed for cataract procedures. These systems can be used for various surgical procedures, including for instance: (1) creating one or more incisions in the cornea or in the limbus to reshape the cornea, (2) creating one or more incisions in the cornea to provide access for a cataract surgery instrument and/or to provide access for implantation of an intraocular lens, (3) incising the anterior lens capsule (anterior capsulotomy) to provide access for removing a cataractous lens, (4) segmenting and/or fragmenting a cataractous lens, and/or (5) incising the posterior lens capsule (posterior capsulotomy) for various cataract-related procedures.

With capsulotomy, the surgeon creates a circular opening in the lens capsule, which is a cellophane-like bag that holds the lens. The incision to create this circular opening is one of the most critical steps of the cataract procedure as its size, shape, and centering may impact the effective positioning of an artificial intraocular lens (IOL) following removal of the cataractous lens. If the artificial lens becomes de-centered or shifts back or forward by even a slight degree, its performance may be diminished leading to refractive error. Laser eye surgery systems for cataract procedures therefore often include imaging systems for more accurate and precise placement of incisions and capsulotomy.

Sometimes, however, to reduce the possibilities of incomplete cutting, a capsulotomy may take longer to perform than is ideal, especially when the scan patterns are substantially longer in a depth dimension than the capsule. Further, slight eye movement and/or lens capsule movement may increase the possibility of an inadequate capsule incision. Hence, laser surgery systems with improved characteristics for intraocular target identification and incision, and related methods, would be beneficial.

SUMMARY

Accordingly, this disclosure provides imaging and/or treatment systems and related methods that can be used in suitable laser surgery systems such as, for example, laser eye surgery systems, that substantially obviate one or more problems due to limitations and disadvantages of the related art. In the special case of a laser-created capsulotomy, the actual target depth requirements is minimal as the anterior lens capsule in humans is only about 7 micro meters thick while the posterior lens capsule is only 3 micro meters thick. The optics used in conventional cataract laser systems have a depth of field of single laser pulses of about 100 micrometers down to 30 micrometers. As such, in principal and in an ideal case, one would only require one single pass of the laser to cut the lens capsule as the material is much thinner than the depth effect of the laser systems. Tissue movements and especially limited alignment and calibration tolerances of the laser systems, however, require that the laser actively cuts several hundreds of micrometers in depth to ensure achieving a complete cut. In some situations, it may be advantageous to treat intraocular targets with a limited number of scans of a treatment laser focal point. This may reduce inadvertent eye/intraocular target movement during or between scans and may reduce the amount of energy delivered to a patient's eye. For example, it may be preferable to provide a capsulotomy with 50 or fewer, 20 or fewer, 10 or fewer, 5 or fewer, and in some cases 3, 2, or fewer scans of a treatment beam. Thus, some methods may adjust a focal point location as the focal point is scanned across the capsule surface. In some situations, the focal point depth may be adjusted after each pulse. In other situations, the focal point depth may be adjusted after a plurality of pulses. Since the focal point of the treatment laser may be continually adjusted to be positioned on an intraocular target, fewer scans may be required to modify and/or treat the target.

In some embodiments of the present invention, methods of modifying an intraocular target are provided. For instance, the intraocular target may be the lens capsule where the capsule is modified by incising the tissue with a treatment beam. The methods may include the step of focusing a treatment beam to a focal point at a first location in the eye, and measuring an intensity signal of electromagnetic radiation reflected from the first location in response to the treatment beam. A second location of the focal point may be identified in the eye using the measured intensity signal of the electromagnetic radiation reflected from the first location. The focal point of the treatment beam may then be scanned toward the second location where tissue at the second location can be altered.

In some embodiments, the method may include a step of scanning a focal point of an imaging beam within the eye and measuring an intensity signal of electromagnetic radiation reflected from focal point locations in response to the imaging beam so as to locate the intraocular target, e.g., the lens capsule of the eye. Thereafter, the treatment beam may be aligned with the located lens capsule. Optionally, the method may include generating the treatment beam and the imaging beam using the same electromagnetic radiation beam source.

In some embodiments, the intensity signal may be measured by a confocal detector. Further, the focal point of the treatment beam may be scanned to a plurality of different locations in the eye. In some embodiments, a depth of the focal point of the treatment beam is dithered. In some embodiments, the focal point may be scanned from a posterior depth toward an anterior depth. Moreover, the focal point of the treatment beam may be scanned in the xy-direction transverse to a direction of beam propagation.

Optionally, the second location may be identified based in part on phase information of the intensity signal. In some embodiments, the second location may be identified by comparing the measured intensity signal to an upper threshold value and a lower threshold value. The identified second location may have a depth less than the depth of the first location when the measured intensity signal of the electromagnetic radiation reflected from the first location is above the upper threshold value. The identified second location may have a depth greater than the depth of the first location where the measured intensity signal of the electromagnetic radiation reflected from the first location is below the lower threshold value. Further, in some embodiments, the identified second location has a depth equal to the depth of the first location when the measured intensity signal of the electromagnetic radiation reflected from the first location is greater than the lower threshold value and less than the upper threshold value.

In some aspects of the invention, a non-transitory computer-readable storage medium including a set of computer executable instructions for modifying an intraocular target of the eye is provided. Execution of the instructions by a computer processor may cause the processor to carry out one or more of the steps described above. In some embodiments, a second location of the focal point may be determined by using a feedback loop based in part on the received intensity signal of the electromagnetic radiation reflected from the focal point at the first location.

In certain aspects of the invention, systems for modifying an intraocular target of the eye are provided. The systems may include an electromagnetic beam source configured to generate a treatment beam and/or an imaging beam. Additionally, the system may include optics configured to focus the treatment beam and/or the imaging beam to a focal point and scan the focal point to locations in the eye. A detector may be configured to receive electromagnetic radiation reflected from the focal point of the treatment beam and to measure an intensity signal of reflected electromagnetic radiation. Furthermore, a controller may be coupled with the beam scanner and the detector and configured to identify a subsequent location of the focal point of the treatment beam using a feedback loop based in part on the measured intensity signal of the electromagnetic radiation reflected from the focal point.

Optionally, the detector may be a confocal detector. In some embodiments, the controller can be configured to dither a depth of the focal point of the treatment beam. The controller may also scan the focal point of the treatment beam from a posterior depth toward an anterior depth so as to avoid beam travel through modified tissue. In some embodiments, the feedback loop may be based in part on phase information of the measured intensity signal.

In some embodiments, the controller may identify the subsequent location of the treatment beam focal point by comparing the measured intensity signal with an upper threshold value with that of a lower threshold value. The identified subsequent location may have a depth less than a depth of the initial focal point location when the measured intensity signal of the electromagnetic radiation reflected from the focal point location is above the upper threshold value. The identified subsequent location may have a depth greater than the depth of the initial focal point location when the measured intensity signal of the electromagnetic radiation reflected from the focal point location is below the lower threshold value. In some embodiments, the system controller may maintain the depth of the treatment beam focal point when the measured intensity signal of the electromagnetic radiation reflected from the focal point is greater than the lower threshold value and less than the upper threshold value.

This summary and the following description are merely exemplary, illustrative, and explanatory, and are not intended to limit, but to provide further explanation of the invention as claimed. Additional features, aspects, objects and advantages of embodiments of this invention are set forth in the descriptions, drawings, and the claims, and in part, will be apparent from the drawings and detailed description, or may be learned by practice. The claims are incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 4, 5, and 6 are simplified block diagrams of optional steps or acts that can be accomplished in the method of FIG. 3 according to many embodiments;

DETAILED DESCRIPTION

The following detailed description describes various embodiments of the present invention. For purposes of explanation, specific configurations and details are set forth so as to provide a thorough understanding of the embodiments. It will also, however, be apparent to one skilled in the art that the present invention can be practiced without the specific details. Furthermore, to avoid obscuring the embodiment being described, various well-known features may be omitted or simplified.

Systems for imaging and/or treating a patient's eye are provided. In many embodiments, a free-floating mechanism provides a variable optical path by which a portion of an electromagnetic beam reflected from a focal point disposed within the eye is directed to a path length insensitive imaging assembly such as a confocal detection assembly. In many embodiments, the free-floating mechanism is configured to accommodate patient eye movement while maintaining alignment between an electromagnetic radiation beam and the eye. The electromagnetic radiation beam can be configured for: (1) imaging the eye; (2) treating the eye; and/or (3) imaging as well as treating the eye.

Figure 1:
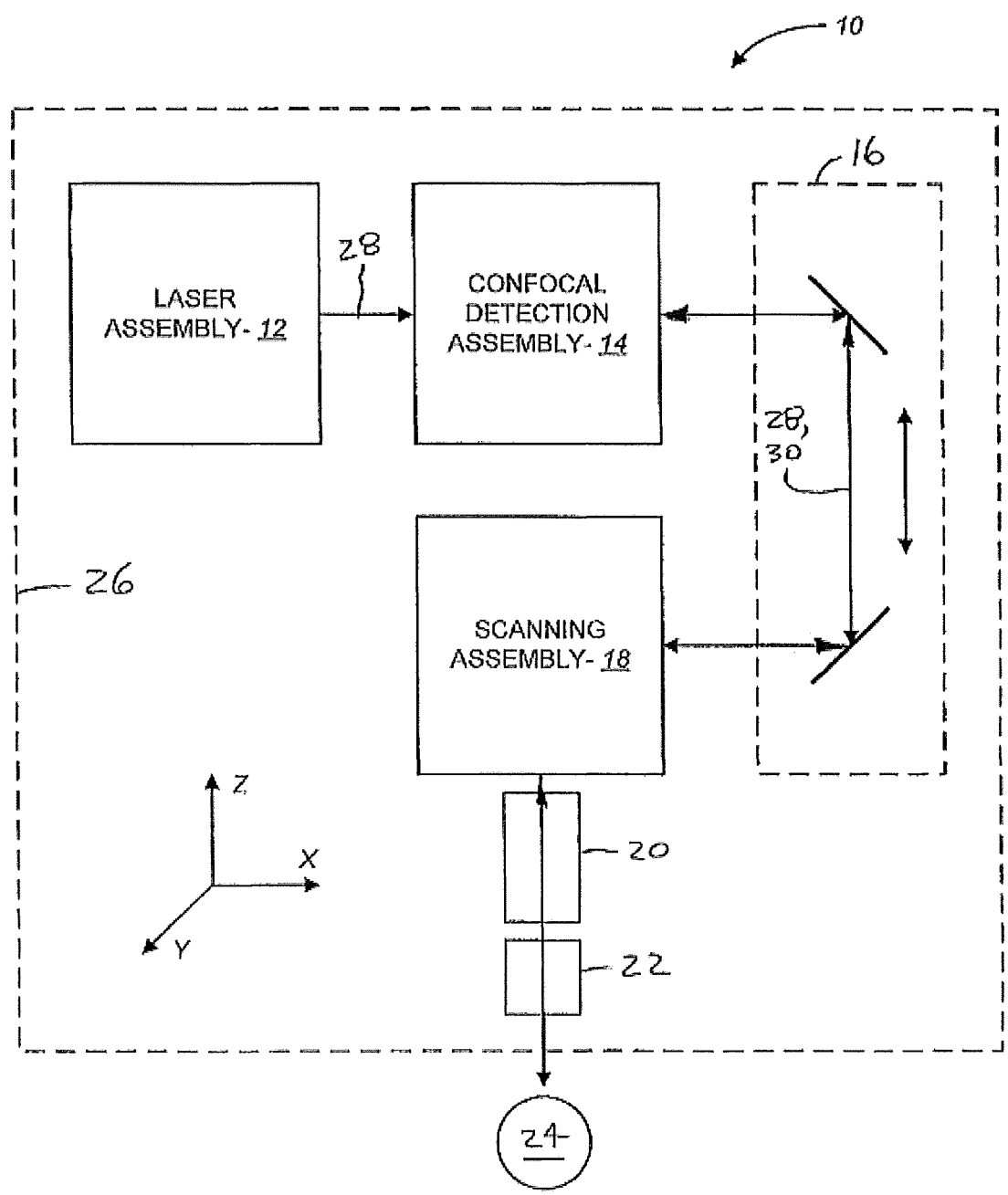
FIG. 1 is a schematic diagram of a laser surgery system according to many embodiments, in which a patient interface device is coupled to a laser assembly and a detection assembly by way of a scanning assembly and a free-floating mechanism that supports the scanning assembly.

Referring now to the drawings in which like numbers reference similar elements, FIG. 1 schematically illustrates a laser surgery system 10, according to many embodiments. The laser surgery system 10 may include a laser assembly 12, a confocal detection assembly 14, a free-floating mechanism 16, a scanning assembly 18, an objective lens assembly 20, and a patient interface device 22. The patient interface device 22 may be configured to interface with a patient 24. The patient interface device 22 may be supported by the objective lens assembly 20, which may be supported by the scanning assembly 18. The scanning assembly 18 may in turn be supported by the free-floating mechanism 16. A portion of the free-floating mechanism 16 may have a fixed position and orientation relative to the laser assembly 12 and the confocal detection assembly 14.

In some embodiments, the patient interface device 22 may be configured to interface with an eye of the patient 24. For example, the patient interface device 22 can be configured to be coupled via vacuum suction to an eye of the patient 24 as described in co-pending U.S. patent application Ser. No.: 14/068,994, entitled "Liquid Optical Interface for Laser Eye Surgery System," filed Oct. 31, 2013, the entire disclosure of which is hereby incorporated by reference. The laser surgery system 10 can further optionally include a base assembly 26 that can be fixed in place or be repositionable. For example, the base assembly 26 can be supported by a support linkage that is configured to allow selective repositioning of the base assembly 26 relative to a patient and to secure the base assembly 26 in a selected fixed position relative to the patient. Such a support linkage can be supported in any suitable manner such as, for example, by a fixed support base or by a movable cart that can be repositioned to a suitable location adjacent to a patient. In many embodiments, the support linkage includes setup joints with each setup joint being configured to permit selective articulation of the setup joint, and can be selectively locked to prevent inadvertent articulation of the setup joint, thereby securing the base assembly 26 in a selected fixed position relative to the patient when the setup joints are locked.

In many embodiments, the laser assembly 12 may be configured to emit an electromagnetic radiation beam 28. The beam 28 can include a series of laser pulses of any suitable energy level, duration, and repetition rate.

In many embodiments, the laser assembly 12 incorporates femtosecond (FS) laser technology. By using femtosecond laser technology, a short duration (e.g., approximately $10^{-13}$ seconds in duration) laser pulse (with energy level in the micro joule range) can be delivered to a tightly focused point to disrupt tissue, thereby substantially lowering the energy level required to image and/or modify an intraocular target as compared to laser pulses having longer durations.

The laser assembly 12 can produce laser pulses having a wavelength suitable to treat and/or to image tissue. For example, the laser assembly 12 can be configured to emit an electromagnetic radiation beam 28 such as that emitted by any of the laser surgery systems described in co-pending U.S. patent application Ser. No. 14/069,044, entitled "Laser Eye Surgery System," filed Oct. 31, 2013; and U.S. patent application Ser. No. 12/987,069, entitled "Method and System For Modifying Eye Tissue and Intraocular Lenses," filed Jan. 7, 2011, the full disclosures of which are incorporated herein by reference. For example, the laser assembly 12 can produce laser pulses having a wavelength in the range of 1020 nm to 1050 nm. For example, the laser assembly 12 can have a diode-pumped solid-state configuration with a 1030 (+/−5) nm center wavelength. As another example, the laser assembly 12 can produce laser pulses having a wavelength in the range of 320 nm to 430 nm. For example, the laser assembly 12 can include an Nd:YAG laser source operating at the 3rd harmonic wavelength (355 nm) and producing pulses having 50 picosecond to 15 nanosecond pulse duration. Depending on the spot size, typical pulse energies used can be in the nano joule to micro joule range. The laser assembly 12 can also include two or more lasers of any suitable configuration.

The laser assembly 12 can include control and conditioning components. For example, such control components can include components such as a beam attenuator to control the energy of the laser pulse and the average power of the pulse train, a fixed aperture to control the cross-sectional spatial extent of the beam containing the laser pulses, one or more power monitors to monitor the flux and repetition rate of the beam train and therefore the energy of the laser pulses, and a shutter to allow/block transmission of the laser pulses. Such conditioning components can include an adjustable zoom assembly and a fixed optical relay to transfer the laser pulses over a distance while accommodating laser pulse beam positional and/or directional variability, thereby providing increased tolerance for component variation.

In many embodiments, the laser assembly 12 and the confocal detection assembly 14 may have fixed positions relative to the base assembly 26. The beam 28 emitted by the laser assembly 12 may propagate along a fixed optical path through the confocal detection assembly 14 to the free-floating mechanism 16. The beam 28 may propagate through the free-floating mechanism 16 along a variable optical path 30, which may deliver the beam 28 to the scanning assembly 18. In many embodiments, the beam 28 emitted by the laser assembly 12 may be collimated so that the beam 28 is not impacted by patient-movement-induced changes in the length of the optical path between the laser assembly 12 and the scanner 16. The scanning assembly 18 may be operable to scan the beam 28 (e.g., via controlled variable deflection of the beam 28) in at least one dimension. In many embodiments, the scanning assembly 18 is operable to scan the beam 28 in two dimensions transverse to the direction of propagation of the beam 28 and may be further operable to scan the location of a focal point of the beam 28 in the direction of propagation of the beam 28. The scanned beam may be emitted from the scanning assembly 18 to propagate through the objective lens assembly 20, through the interface device 22, and to the patient 24.

The free-floating mechanism 16 may be configured to accommodate a range of movement of the patient 24 relative to the laser assembly 12 and the confocal detection assembly 14 in one or more directions while maintaining alignment of the beam 28 emitted by the scanning assembly 18 with the patient 24. For example, in many embodiments, the free-floating mechanism 16 may be configured to accommodate a range movement of the patient 24 in any direction defined by any combination of unit orthogonal directions (X, Y, and Z).

The free-floating mechanism 16 may support the scanning assembly 18 and may provide the variable optical path 30, which may change in response to movement of the patient 24. Because the patient interface device 22 may be interfaced with the patient 24, movement of the patient 24 may result in corresponding movement of the patient interface device 22, the objective lens assembly 20, and the scanning assembly 18. The free-floating mechanism 16 can include, for example, any suitable combination of a linkage that accommodates relative movement between the scanning assembly 18 and, for example, the confocal detection assembly 24, and optical components suitably tied to the linkage so as to form the variable optical path 30. Optionally, the free-floating mechanism 16 can be configured as described in U.S. Provisional Patent Application 61/780,736 filed Mar. 13, 2013, entitled "Laser Surgery System," the entire disclosure of which is incorporated herein by reference.

A portion of the electromagnetic radiation beam 28 may reflect from an eye tissue at the focal point and may propagate back to the confocal detection assembly 14. Specifically, a reflected portion of the electromagnetic radiation beam 28 may travel back through the patient interface device 22, back through the objective lens assembly 20, back through (and de-scanned by) the scanning assembly 18, back through the free-floating mechanism 16 (along the variable optical path 30), and to the confocal detection assembly 14. In many embodiments, the reflected portion of the electromagnetic radiation beam that travels back to the confocal detection assembly 14 may be directed to be incident upon a sensor that generates an intensity signal indicative of intensity of the incident portion of the electromagnetic radiation beam. The intensity signal, coupled with associated scanning of the focal point within the eye, can be processed in conjunction with the parameters of the scanning to, for example, image/locate structures of the eye, such as the anterior surface of the cornea, the posterior surface of the cornea, the iris, the anterior surface of the lens capsule, and the posterior surface of the lens capsule. In many embodiments, the amount of the reflected electromagnetic radiation beam that travels to the confocal detection assembly 14 may be substantially independent of expected variations in the length of the variable optical path 30 due to patient movement, thereby enabling the ability to ignore patient movements when processing the intensity signal to image/locate structures of the eye.

Figure 2:
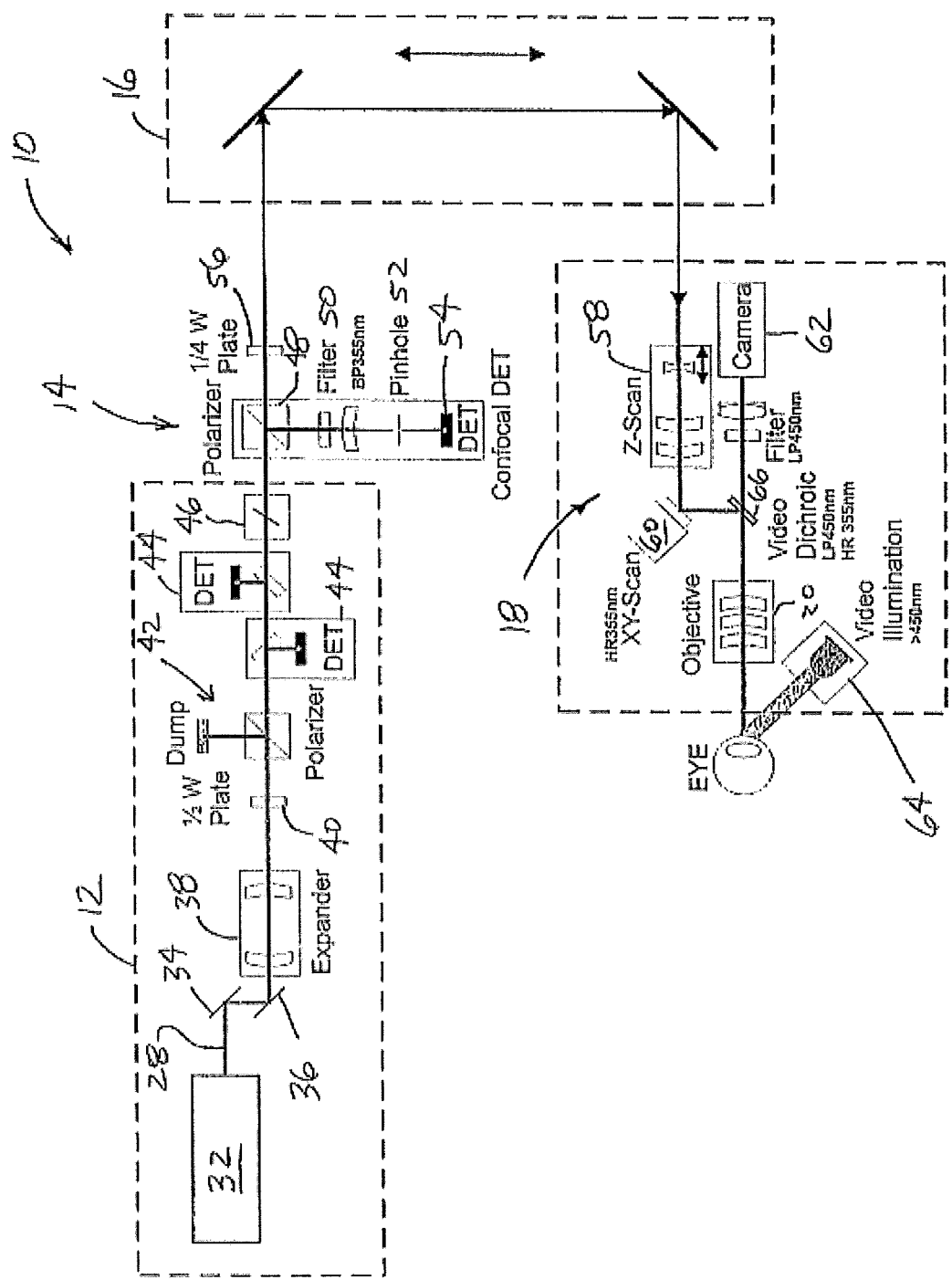
FIG. 2 is a schematic diagram of an embodiment of the laser surgery system of FIG. 1.

FIG. 2 schematically illustrates details of an embodiment of the laser surgery system 10. Specifically, example configurations are schematically illustrated for the laser assembly 12, the confocal detection assembly 14, and the scanning assembly 18. As shown in the illustrated embodiment, the laser assembly 12 can include an ultrafast (UF) laser 32 (e.g., a femtosecond laser), alignment mirrors 34, 36, a beam expander 38, a one-half wave plate 40, a polarizer and beam dump device 42, output pickoffs and monitors 44, and a system-controlled shutter 46. The electromagnetic radiation beam 28 output by the laser 32 may be deflected by the alignment mirrors 34, 36. In many embodiments, the alignment mirrors 34, 36 may be adjustable in position and/or orientation so as to provide the ability to align the beam 28 with the downstream optical path through the downstream optical components. Next, the beam 28 may pass through the beam expander 38, which can increase the diameter of the beam 28. Next, the expanded beam 28 may pass through the one-half wave plate 40 before passing through the polarizer. The beam exiting the laser may be linearly polarized. The one-half wave plate 40 can rotate this polarization. The amount of light passing through the polarizer depends on the angle of the rotation of the linear polarization. Therefore, the one-half wave plate 40 with the polarizer may act as an attenuator of the beam 28. The light rejected from this attenuation may be directed into the beam dump. Next, the attenuated beam 28 may pass through the output pickoffs and monitors 44 and then through the system-controlled shutter 46. By locating the system-controlled shutter 46 downstream of the output pickoffs and monitors 44, the power of the beam 28 can be checked before opening the system-controlled shutter 46.

As shown in the illustrated embodiment, the confocal detection assembly 14 can include a polarization-sensitive device such as a polarized or an unpolarized beam splitter 48, a filter 50, a focusing lens 51, a pinhole aperture 52, and a detection sensor 54. A one-quarter wave plate 56 may be disposed downstream of the polarized beam splitter 48. The beam 28 as received from the laser assembly 12 may be polarized so as to pass through the polarized beam splitter 48. Next, the beam 28 may pass through the one-quarter wave plate 56, thereby rotating the polarization axis of the beam 28. A quarter rotation may be a preferred rotation amount. After reflecting from a focal point in the eye, a returning reflected portion of the beam 28 may pass back through the one-quarter wave plate 56, thereby further rotating the polarization axis of the returning reflected portion of the beam 28. After passing back through the one-quarter wave plate 56, the returning reflected portion of the beam may experience a total polarization rotation of 90 degrees so that the reflected light from the eye may be fully reflected by the polarized beam splitter 48. A birefringence of the cornea can also be taken into account if, for example, the imaged structure is the lens. In such a case, the plate 56 can be adjusted/configured so that the double pass of the plate 56 as well as the double pass of the cornea sum up to a polarization rotation of 90 degrees. Because the birefringence of the cornea may be different form patient to patient, the configuration/adjustment of the plate 56 can be done dynamically so as to optimize the signal returning to the detection sensor 54. In some embodiments, the plate 56 may be rotated an angle. Accordingly, the returning reflected portion of the beam 28 may be polarized to be at least partially reflected by the polarized beam splitter 48 so as to be directed through the filter 50, through the lens 51, and to the pinhole aperture 52. The filter 50 can be configured to block wavelengths other than the wavelengths of interest. The pinhole aperture 52 may block any returning reflected portion of the beam 28 reflected from locations other than the focal point from reaching the detection sensor 54. Because the amount of returning reflected portion of the beam 28 that reaches the detection sensor 54 depends upon the nature of the tissue at the focal point of the beam 28, the signal generated by the detection sensor 54 can be processed in combination with data regarding the associated locations of the focal point so as to generate image/location data for structures of the eye.

As shown in the illustrated embodiment, the scanning assembly 18 can include a z-scan device 58 and a xy-scan device 60. The z-scan device 58 may be operable to vary a convergence/divergence angle of the beam 28 and thereby change a location of the focal point in the direction of propagation of the beam 28. For example, the z-scan device 58 can include one or more lenses that are controllably movable in the direction of propagation of the beam 28 to vary a convergence/divergence angle of the beam 28. The xy-scan device 60 may be operable to deflect the beam 28 in two dimensions transverse to the direction of propagation of the beam 28. For example, the xy-scan device 60 can include one or more mirrors that are controllably deflectable to scan the beam 28 in two dimensions transverse to the direction of propagation of the beam 28. Accordingly, the combination of the z-scan device 58 and the xy-scan device 60 can be operated to controllably scan the focal point in three dimensions, for example, within the eye of the patient.

As shown in the illustrated embodiment, a camera 62 and associated video illumination 64 can be integrated with the scanning assembly 18. The camera 62 and the beam 28 may share a common optical path through the objective lens assembly 20 to the eye. A video dichroic 66 may be used to combine/separate the beam 28 with/from the illumination wavelengths used by the camera. For example, the beam 28 can have a wavelength of about 355 nm and the video illumination 64 can be configured to emit illumination having wavelengths greater than 450 nm. Accordingly, the video dichroic 66 can be configured to reflect the 355 nm wavelength while transmitting wavelengths greater than 450 nm.

Figure 3:
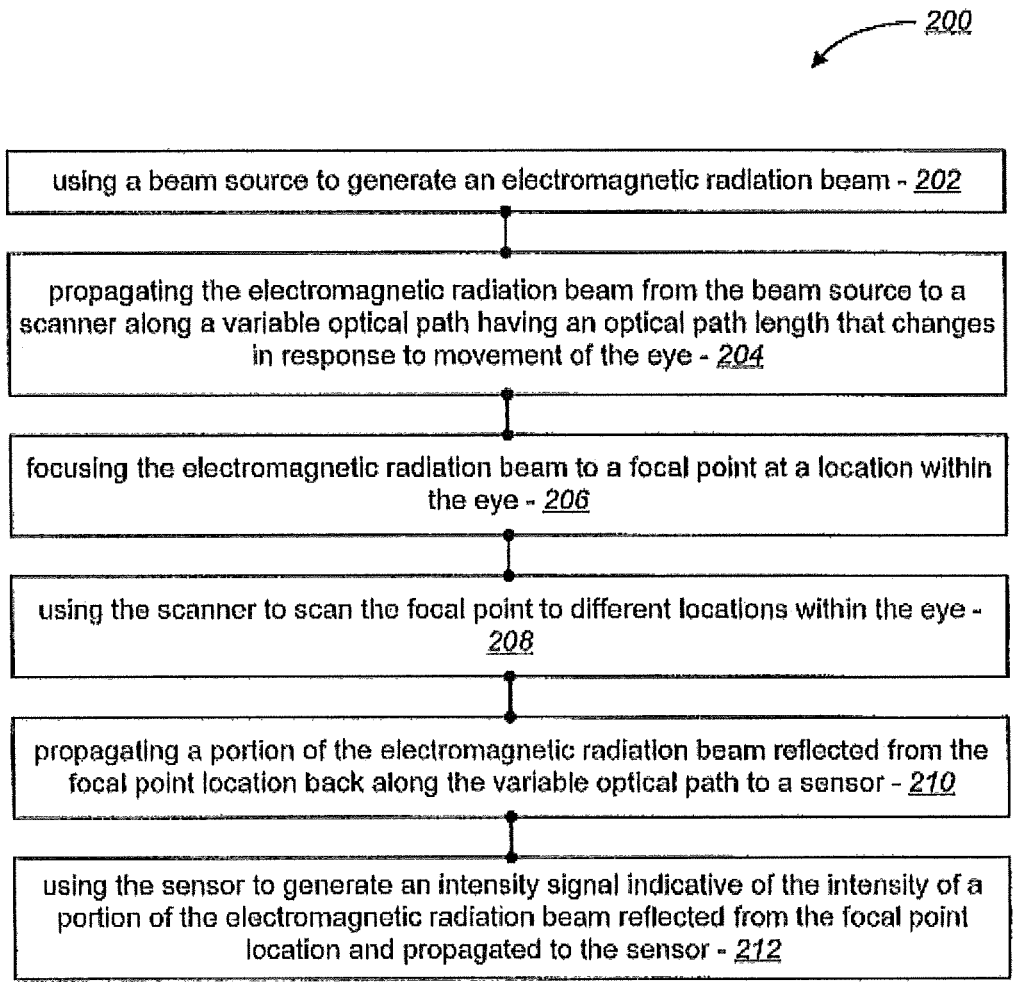
FIG. 3 is a simplified block diagram of steps of a method of imaging and/or modifying an intraocular target according to many embodiments.

FIG. 3 is a simplified block diagram of acts of a method 200, according to many embodiments, of imaging an eye. Any suitable device, assembly, and/or system, such as described herein, can be used to practice the method 200. The method 200 may include using a beam source to generate an electromagnetic radiation beam (act 202).

The method 200 may include propagating the electromagnetic radiation beam from a beam source to a scanner along a variable optical path having an optical path length that changes in response to movement of the eye (act 204). The method 200 may include focusing the electromagnetic radiation beam to a focal point at a location within the eye (act 206). The method 200 may include using the scanner to scan the focal point to different locations within the eye (act 208). The method 200 may include propagating a portion of the electromagnetic radiation beam reflected from the focal point location back along the variable optical path to a sensor (act 210). The method 200 may include using the sensor to generate an intensity signal indicative of the intensity of a portion of the electromagnetic radiation beam reflected from the focal point location and propagated to the sensor (act 212).

Figure 4:
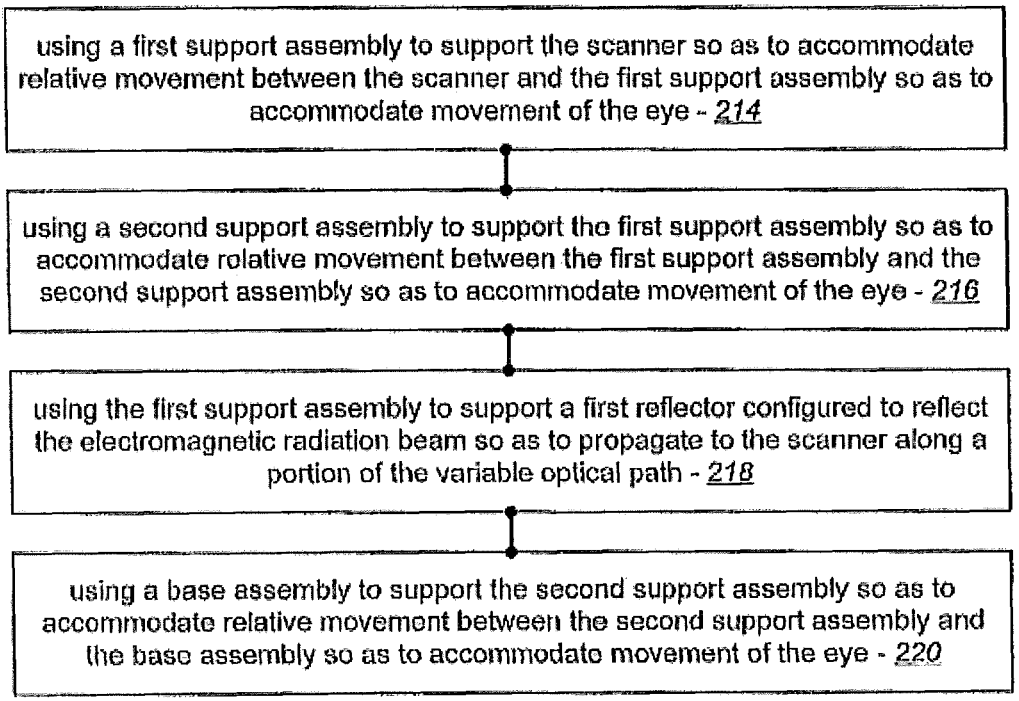

FIGS. 4, 5, and 6 are simplified block diagrams of optional steps or acts that can be accomplished as part of the method 200. For example, the method 200 can include using a first support assembly to support the scanner so as to accommodate relative movement between the scanner and the first support assembly so as to accommodate movement of the eye (act 214). The method 200 can include using a second support assembly to support the first support assembly so as to accommodate relative movement between the first support assembly and the second support assembly so as to accommodate movement of the eye (act 216). The method 200 can include using the first support assembly to support a first reflector configured to reflect the electromagnetic radiation beam so as to propagate to the scanner along a portion of the variable optical path (act 218). The method 200 can include using a base assembly to support the second support assembly so as to accommodate relative movement between the second support assembly and the base assembly so as to accommodate movement of the eye (act 220). The method 200 can include using the second support assembly to support a second reflector configured to reflect the electromagnetic radiation beam to propagate along a portion of the variable optical path so as to be incident on the first reflector (act 222). The method 200 can include using the sensor to generate the intensity signal comprises passing a reflected portion of the electromagnetic radiation beam through an aperture to block portions of the electromagnetic radiation beam reflected from locations other than the focal point location (act 224). The method 200 can include passing the electromagnetic radiation beam through a polarization-sensitive device (act 226). The method 200 can include modifying polarization of at least one of the electromagnetic radiation beam and a portion of the electromagnetic radiation beam reflected from the focal point location (act 228). The method 200 can include using the polarization-sensitive device to reflect a portion of the electromagnetic radiation beam reflected from the focal point location so as to be incident upon the sensor (act 230).

Figure 7:
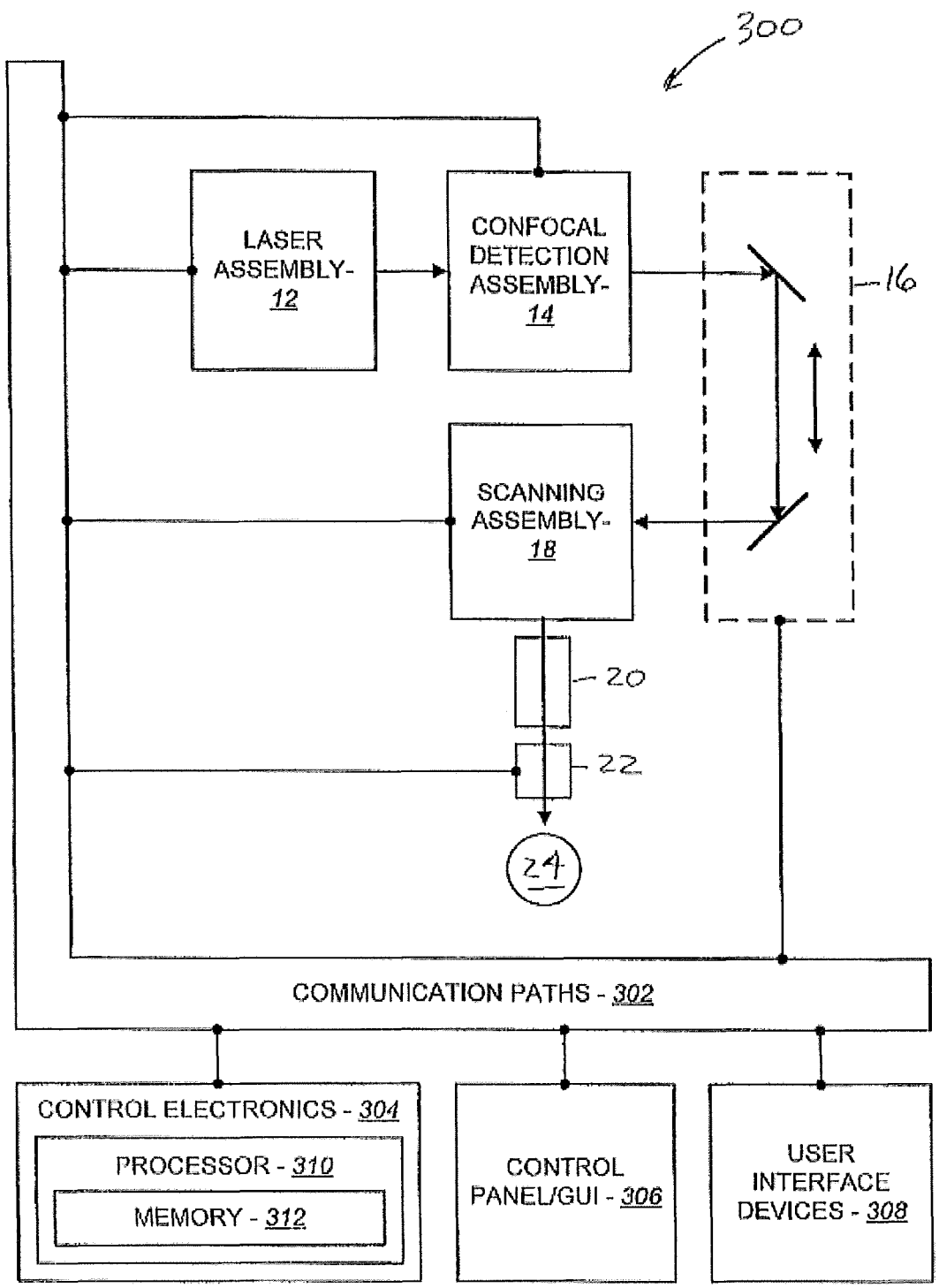
FIG. 7 is a schematic diagram of an embodiment of the laser surgery system of FIG. 1.

FIG. 7 schematically illustrates a laser surgery system 300 according to many embodiments. The laser surgery system 300 includes the laser assembly 12, the confocal detection assembly 14, the free-floating mechanism 16, the scanning assembly 18, the objective lens assembly 20, the patient interface 22, communication paths 302, control electronics 304, control panel/graphical user interface (GUI) 306, and user interface devices 308. The control electronics 304 includes processor 310, which includes memory 312. The patient interface 22 is configured to interface with a patient 24. The control electronics 304 is operatively coupled via the communication paths 302 with the laser assembly 12, the confocal detection assembly 14, the free-floating mechanism 16, the scanning assembly 18, the control panel/GUI 306, and the user interface devices 308.

The scanning assembly 18 can include a z-scan device and a xy-scan device. The laser surgery system 300 can be configured to focus the electromagnetic radiation beam 28 to a focal point that is scanned in three dimensions. The z-scan device can be operable to vary the location of the focal point in the direction of propagation of the beam 28. The xy-scan device can be operable to scan the location of the focal point in two dimensions transverse to the direction of propagation of the beam 28. Accordingly, the combination of the z-scan device and the xy-scan device can be operated to controllably scan the focal point of the beam in three dimensions, including: within a tissue of the patient 24 such as within an eye tissue of the patient 24. The scanning assembly 18 may be supported by the free-floating mechanism 16, which may accommodate patient movement induced movement of the scanning assembly 18 relative to the laser assembly 12 and the confocal detection assembly 14 in three dimensions.

The patient interface 22 is coupled to the patient 24 such that the patient interface 22, the objective lens assembly 20, and the scanning assembly 18 move in conjunction with the patient 24. For example, in many embodiments, the patient interface 22 employs a suction ring that is vacuum attached to an eye of the patient 24. The suction ring can be coupled with the patient interface 22, for example, using vacuum to secure the suction ring to the patient interface 22.

The control electronics 304 controls the operation of and/or can receive input from the laser assembly 12, the confocal detection assembly 14, the free-floating assembly 16, the scanning assembly 18, the patient interface 22, the control panel/GUI 306, and the user interface devices 308 via the communication paths 302. The communication paths 302 can be implemented in any suitable configuration, including any suitable shared or dedicated communication paths between the control electronics 304 and the respective system components.

The control electronics 304 can include any suitable components, such as one or more processor, one or more field-programmable gate array (FPGA), and one or more memory storage devices. In many embodiments, the control electronics 304 controls the control panel/GUI 306 to provide for pre-procedure planning according to user specified treatment parameters as well as to provide user control over the laser eye surgery procedure.

The control electronics 304 can include a processor/controller 310 that is used to perform calculations related to system operation and provide control signals to the various system elements. A computer readable medium 312 is coupled to the processor 310 in order to store data used by the processor and other system elements. The processor 310 interacts with the other components of the system as described more fully throughout the present specification. In an embodiment, the memory 312 can include a look up table that can be utilized to control one or more components of the laser system surgery system 300.

The processor 310 can be a general purpose microprocessor configured to execute instructions and data, such as a Pentium processor manufactured by the Intel Corporation of Santa Clara, Calif. It can also be an Application Specific Integrated Circuit (ASIC) that embodies at least part of the instructions for performing the method according to the embodiments of the present disclosure in software, firmware and/or hardware. As an example, such processors include dedicated circuitry, ASICs, combinatorial logic, other programmable processors, any combinations thereof, and the like.

The memory 312 can be local or distributed as appropriate to the particular application. Memory 312 can include a number of memories including a main random access memory (RAM) for storage of instructions and data during program execution and a read only memory (ROM) in which fixed instructions are stored. Thus, the memory 312 provides persistent (non-volatile) storage for program and data files, and may include a hard disk drive, flash memory, a floppy disk drive along with associated removable media, a Compact Disk Read Only Memory (CD-ROM) drive, an optical drive, removable media cartridges, and other like storage media.

The user interface devices 308 can include any suitable user input device suitable to provide user input to the control electronics 304. For example, the user interface devices 308 can include devices such as, for example, a touch-screen display/input device, a keyboard, a footswitch, a keypad, a patient interface radio frequency identification (RFID) reader, an emergency stop button, and a key switch.

Focal Point Scan Control

Figure 8:
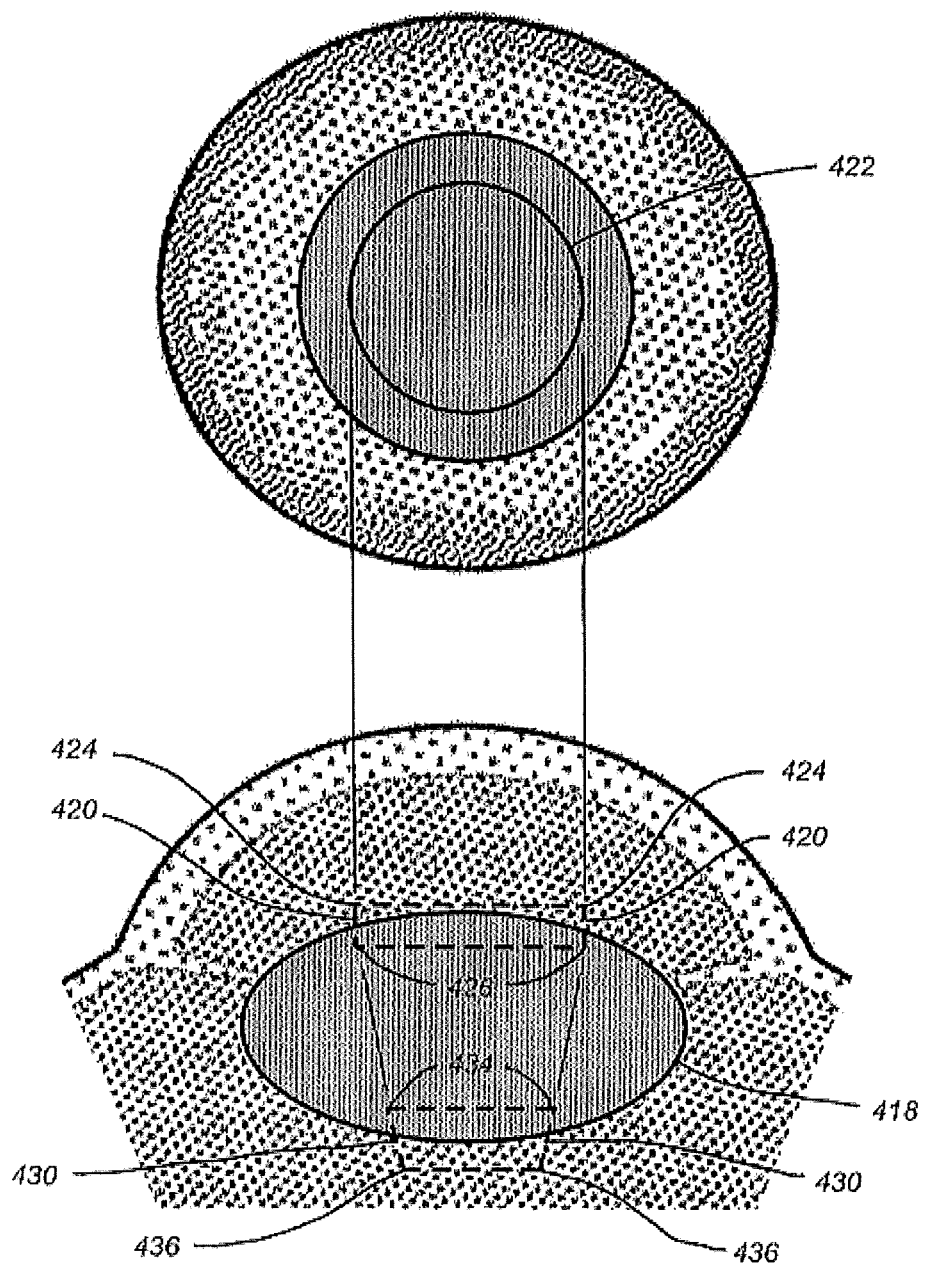
FIG. 8 shows a plan view of a capsulotomy incision locator and a cross-sectional view showing a projection of the capsulotomy incision locator on the lens anterior capsule according to many embodiments.
Figure 9:
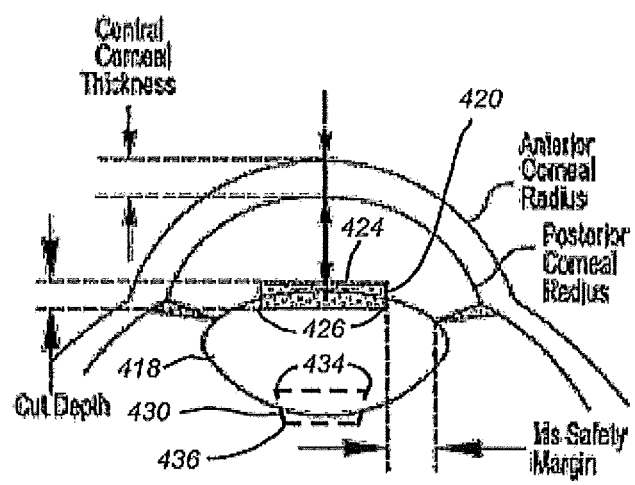
FIG. 9 shows a cross-sectional view of an eye and a capsulotomy incision region defining a closed boundary incision surface transecting the lens anterior capsule according to many embodiments.

The laser surgery system 10 can be configured to image and/or modify an intraocular target by scanning the focal point of the electromagnetic radiation beam in a particular area. For example, referring now to FIG. 8 and FIG. 9, the laser surgery system 10 can be used to incise an anterior capsulotomy and/or a posterior capsulotomy in the anterior portion of a lens capsule 418. The focal point of the electromagnetic radiation beam can be scanned to form an anterior capsulotomy closed incision boundary surface 420 that transects the anterior portion of the lens capsule 418. Likewise, the focal point of the electromagnetic radiation beam can be scanned to form a posterior capsulotomy closed incision boundary surface 430 that transects the posterior portion of the lens capsule 418.

The anterior and/or posterior closed incision boundary surfaces 420, 430 can be designated using any suitable approach. For example, a plan view of the patient's eye can be obtained using the camera 62. A capsulotomy incision designator 422 can be located and shown superimposed on the plan view of the patient's eye to illustrate the size, location, and shape of a planned capsulotomy relative to the patient's eye. The capsulotomy incision designator 422 can be manually defined by an operator of the laser surgery system 10 and/or the laser surgery system 10 can be configured to generate an initial capsulotomy incision designator 422 for operator verification and/or modification.

Figure 10:
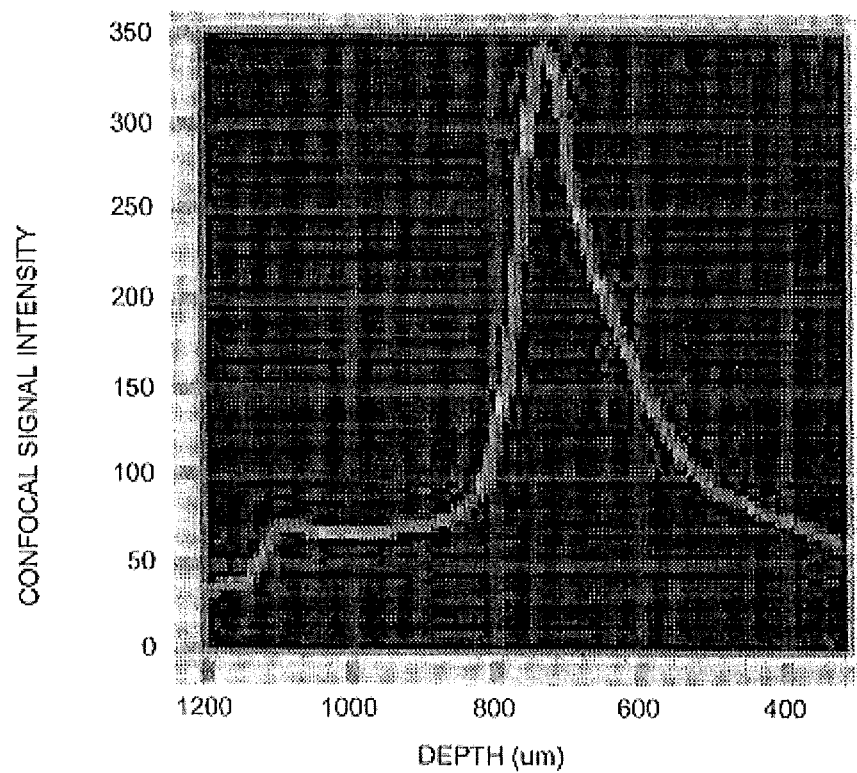
FIG. 10 illustrates variation in intensity of a signal generated while scanning the focal point of the electromagnetic radiation beam in a scan pattern that crosses a boundary of an intraocular target according to many embodiments.

The anterior capsulotomy closed incision boundary surface 420 can be defined on a projection of the capsulotomy incision designator 422 such that the anterior capsulotomy closed incision boundary surface 420 transects the anterior portion of the lens capsule 418 at all locations around the anterior capsulotomy incision boundary surface 420 for all expected variations in the location of the anterior portion of the lens capsule 418 relative to the projection of the capsulotomy incision designator 422. For example, a curve corresponding to the capsulotomy incision designator 422 can be projected to define an intersection with a minimum depth mathematical surface model (e.g., a spherical surface) defining a minimum expected depth configuration for the anterior portion of the lens capsule 418 with the resulting intersection being an anterior capsulotomy upper closed curve 424 that defines an upper boundary for the anterior capsulotomy closed incision boundary surface 420. Likewise, the curve corresponding to the capsulotomy incision designator 422 can be projected to define an intersection with a maximum depth mathematical surface model (e.g., a spherical surface) defining a maximum expected depth configuration for the anterior portion of the lens capsule 418 with the resulting intersection being an anterior capsulotomy lower closed curve 426 that defines a lower boundary for the anterior capsulotomy closed incision boundary surface 420. Alternatively, the focal point can be scanned using a low imaging-only power level (e.g., a power level sufficient to provide for imaging of the intraocular target via processing of the signal generated by the detection sensor 54 of the confocal detection assembly 14 without modifying the intraocular target) along the projection of the capsulotomy incision designator 422 while varying the depth of the focal point to determine the depth of the anterior lens capsule at a sufficient number of locations around the projection of the capsulotomy incision designator 422. For example, FIG. 10 illustrates variation of intensity of the signal generated by the detection sensor 54 with variation in depth of the focal point with the maximum peak in intensity corresponding to the depth of the anterior portion of the lens. The measured depths of the anterior lens can then be used to determine suitable anterior capsulotomy upper and lower boundary curves 424, 426 of the anterior capsulotomy closed incision boundary surface 420.

In a similar fashion, the posterior capsulotomy closed incision boundary surface 430 can be defined on a projection of the capsulotomy incision designator 422 such that the posterior capsulotomy closed incision boundary surface 430 transects the posterior portion of the lens capsule 418 at all locations around the posterior capsulotomy incision boundary surface 430 for all expected variations in the location of the posterior portion of the lens capsule 418 relative to the projection of the capsulotomy incision designator 422. For example, the curve corresponding to the capsulotomy incision designator 422 can be projected to define an intersection with a minimum depth mathematical surface model (e.g., a spherical surface) defining a minimum expected depth configuration for the posterior portion of the lens capsule 418 with the resulting intersection being a posterior capsulotomy upper closed curve 434 that defines an upper boundary for the posterior capsulotomy closed incision boundary surface 430. Likewise, the curve corresponding to the capsulotomy incision designator 422 can be projected to define an intersection with a maximum depth mathematical surface model (e.g., a spherical surface) defining a maximum expected depth configuration for the posterior portion of the lens capsule 418 with the resulting intersection being a posterior capsulotomy lower closed curve 436 that defines a lower boundary for the posterior capsulotomy closed incision boundary surface 430. Alternatively, the focal point can be scanned using a low imaging-only power level (e.g., a power level sufficient to provide for imaging of the intraocular target via processing of the signal generated by the detection sensor 54 of the confocal detection assembly 14 without modifying the intraocular target) along the projection of the capsulotomy incision designator 422 while varying the depth of the focal point to determine the depth of the posterior lens capsule at a sufficient number of locations around the projection of the capsulotomy incision designator 422. The measured depths of the posterior lens capsule can then be used to determine suitable posterior capsulotomy upper and lower boundary curves 434, 436 of the posterior capsulotomy closed incision boundary surface 430.

While any suitable projection of the capsulotomy incision designator 422 can be used to define the anterior and/or posterior capsulotomy incision boundary surfaces 420, 430, in many embodiments an inverted cone shaped projection of the capsulotomy incision designator 422 is employed so as to maintain a suitable safety margin distance between the electromagnetic radiation beam, which converges to the focal point while propagating from the objective lens assembly 20 to the focal point, and the edge of the iris. Accordingly, in many embodiments, the posterior capsulotomy has a smaller diameter than a corresponding anterior capsulotomy for a given capsulotomy incision designator 422, for example, as illustrated.

The laser surgery system 10 can be used to form any suitably-shaped capsulotomy. For example, while the anterior and the posterior capsulotomies in the illustrated embodiments are circular, any other suitable shape, including but not limited to, elliptical, rectangular, and polygonal can be formed. And, the anterior and/or the posterior capsulotomy can be shaped to accommodate any correspondingly suitably-shaped intraocular lens (IOL).

Concurrent Imaging and Adaptive Tissue Treatment

The laser surgery system 10 can be configured to generate image data concurrent with tissue treatment. For example, the focal point of the electromagnetic radiation beam can have an intensity sufficient to modify an intraocular target (e.g., eye tissue, an IOL) with a resulting portion of the electromagnetic radiation beam reflected from the focal point back to the detection sensor 54 of confocal detection assembly 14 used to generate a signal that is processed to generate image data corresponding to the focal point location.

By scanning the focal point in a pattern that crosses a boundary of an intraocular target, the detection sensor 54 can be used to concurrently generate a signal that can be processed to identify the location of the crossed boundary. For example, FIG. 10 illustrates variation of intensity of the signal generated by the detection sensor 54 with variation in depth of the focal point with the maximum peak in intensity corresponding to the depth of the anterior portion of the lens. The location of the crossed boundary can be used to control subsequent scanning of the focal point so as to reduce the amount of tissue that is treated. For example, when incising an anterior capsulotomy in the lens capsule, the focal point can be scanned in a scan pattern that is at least in part based on the location of the anterior portion of the lens as determined by processing the signal from the detection sensor 54 generated during a previous scan pattern.

Figure 11:
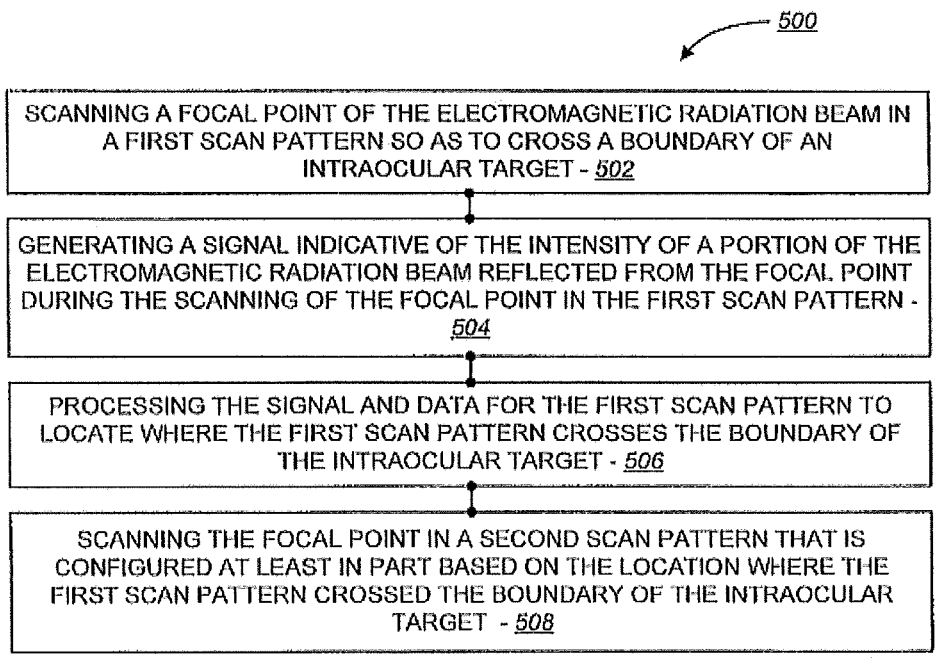
FIG. 11 is a simplified block diagram of steps or acts of a method for adaptively scanning the focal point of the electromagnetic radiation beam relative to a boundary of an intraocular target according to many embodiments.

FIG. 11 is a simplified block diagram of acts of a method 500 for adaptively scanning the focal point of the electronic radiation beam relative to a boundary of an intraocular target, according to many embodiments. The method 500 can be accomplished, for example, using any suitable system including any suitable laser surgery system described herein such as the laser surgery system 10.

The method 500 includes scanning a focal point of the electromagnetic radiation beam in a first scan pattern so as to cross a boundary of an intraocular target (act 502). In many embodiments, the scan pattern moves the focal point transverse to and/or parallel to the direction of propagation of the electromagnetic radiation beam. The intraocular target having the crossed boundary can be any suitable intraocular target including, for example, the anterior lens capsule, the posterior lens capsule, the crystalline lens, the cornea, the iris, an intraocular lens, and the limbus. Where a plurality of scan patterns is applied to create an incision surface (e.g., the closed incision boundary surface 420 shown in FIGS. 8 and 9), the scan patterns can be configured such that the electromagnetic radiation beam propagates to the focal point through unmodified eye tissue and/or IOL material. For example, the scan patterns can be configured and accomplished such that modification occurs in a generally deeper to shallower manner (e.g., posterior to anterior).

The method 500 further includes generating a signal indicative of the intensity of a portion of the electromagnetic radiation beam reflected from the focal point during the scanning of the focal point in the first scan pattern (act 504). For example, because the first scan pattern crosses the boundary of the intraocular target, the signal generated by the detection sensor (e.g., such as the signal illustrated in FIG. 10) and focal point position data for the first scan pattern can be processed to determine the location of the crossed boundary (act 506) by, for example, identifying a signal variation consistent with the applicable boundary.

Having determined the location of where the first scan pattern crossed the boundary of the intraocular target, the focal point can be scanned in a second scan pattern that is configured at least in part based on the location where the first scan pattern crossed the boundary of the intraocular target (act 508). For example, the second scan pattern can be configured to only extend beyond an estimated location of where the second scan pattern will cross the boundary of the intraocular target by predetermined amounts selected to account for possible variations in the estimated location of where the second scan pattern will cross the boundary in view of knowing where the first scan pattern crossed the boundary of the intraocular target. In many embodiments, the second scan pattern will be immediately adjacent to if not overlapped with the first scan pattern, thereby reducing the possible variation between the measured location where the first scan pattern crossed the boundary and the estimated location where the second scan pattern will cross the boundary. In many embodiments in which an incision surface is created, a series of subsequent scan patterns can be accomplished in which the location where one or more previous scan patterns crossed the boundary of the intraocular lens can be used to configured at least one of the subsequent scan patterns to, for example, minimize the tissue and/or material modified and/or increase the accuracy with regard to which tissue and/or material is modified.

Figure 12:
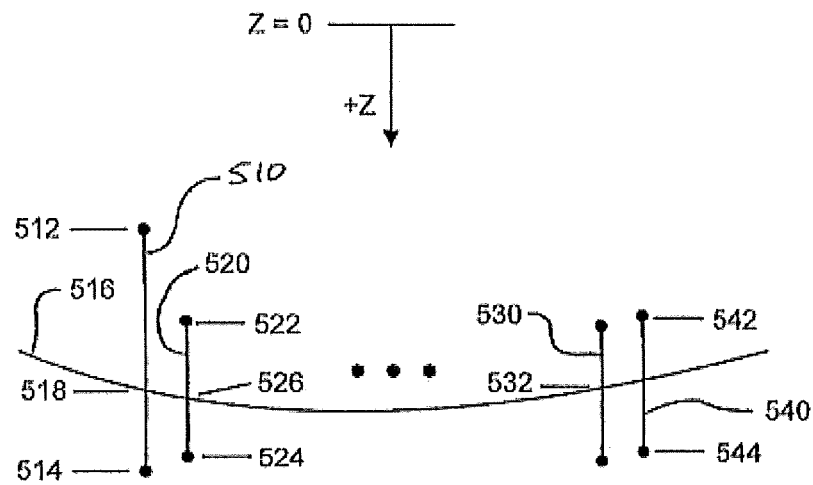
FIG. 12 is a schematic diagram illustrating repeatedly using a location of where a scan pattern for the focal point crosses a boundary of an intraocular target to determine upper and/or lower depth limits for a subsequent scan pattern for the focal point according to many embodiments.

FIG. 12 schematically illustrates repeated use of a location where a scan pattern for the focal point crossed a boundary of an intraocular target to configure a subsequent scan pattern. While FIG. 12 employs scan patterns having variation in the location of the focal point relative to the z-dimension (i.e., parallel to the direction of propagation of the electromagnetic radiation beam), the concept illustrated can be adapted to apply to any suitable scan pattern having, for example, variation in the location of the focal point relative to directions transverse to as well as transverse to and parallel to the direction of propagation of the electromagnetic radiation beam (e.g., x-direction variation, y-direction variation, and/or z-direction variation). An initial scan pattern 510 can be configured so as to extend between two locations 512,514 that are selected so that the initial scan pattern 510 crosses a boundary 516 for an intraocular target for all expected variations in the location of the boundary 516. By processing the signal generated by the detection sensor 54 during the initial scan pattern 510 along with focal point location data for the initial scan pattern 510, a location 518 where the initial scan pattern 510 crossed the boundary 516 can be identified.

A second scan pattern 520 can then be configured at least in part based on the location 518. For example, end locations 522, 524 for the second scan pattern 520 can be selected based on the location 518 so as to, for example, substantially minimize the length of the second scan pattern so as to minimize the amount of tissue and/or material treated. By processing the signal generated by the detection sensor 54 during the second scan pattern 520 along with focal point location data for the second scan pattern 520, a location 526 where the second scan pattern 520 crossed the boundary 516 can be identified.

Any suitable subsequent scan pattern can be configured in a similar fashion. For example, by processing the signal generated by the detection sensor during a scan pattern 530 along with focal point location data tor the scan pattern 530, a location 532 where the scan pattern 530 crossed the boundary 516 can be identified. End points 542, 544 for a subsequent scan pattern 540 can be selected based on the location 532 so as to, for example, substantially minimize the length of the scan pattern 540 so as to minimize the amount of tissue and/or material treated. Accordingly, a series of scan patterns can be adaptively configured and applied using boundary location data for the intraocular target generated from one or more previous scan patterns.

Figure 13:
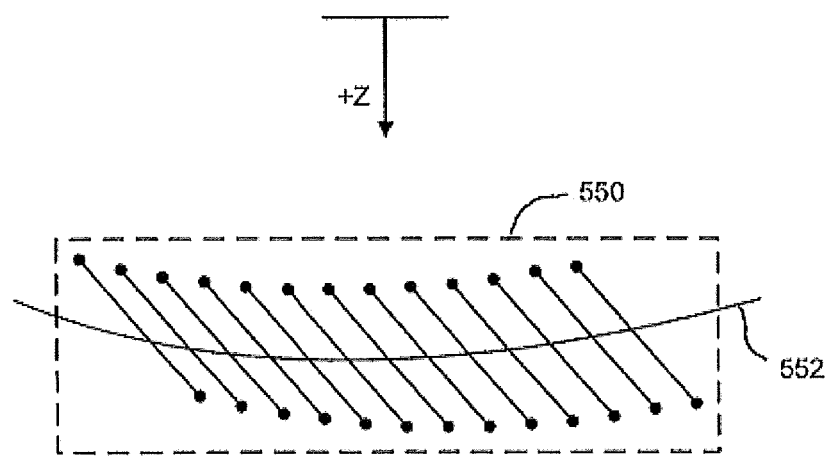
FIG. 13 is a schematic diagram illustrating a series of scan patterns that can be used to incise a surface that transects a boundary of an intraocular target according to many embodiments.

FIG. 13 illustrates a series of scan patterns 550 that can be used to incise a surface that transects a boundary 552 of an intraocular target. In the illustrated embodiment, the scan patterns 550 are adaptively configured using boundary location data generated from one or more previous scan patterns of the series of scan patterns 550, such as described above with respect to FIG. 12 and method 500. Accordingly, the series of scan patterns 550 can be configured to generally extend beyond both sides of the boundary 552 by substantially uniform distances and thereby follow the general shape of the boundary 552.

Figure 14:
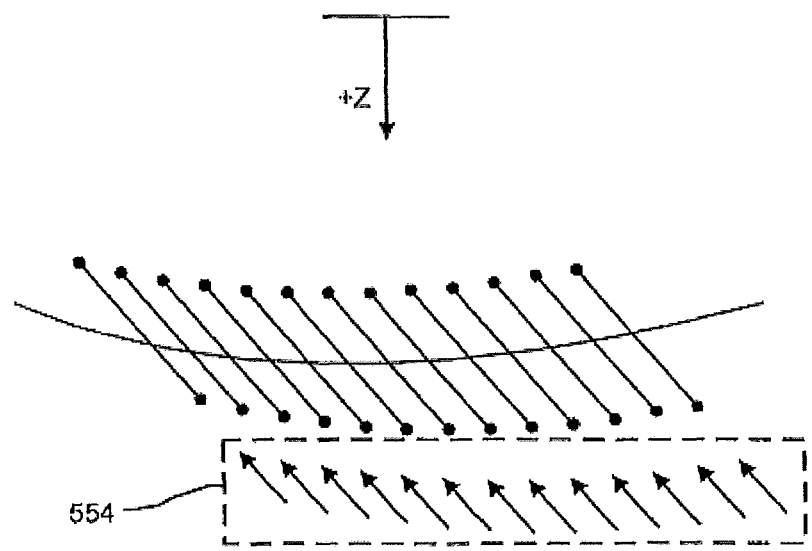
FIG. 14 and FIG. 15 are schematic diagrams illustrating embodiments of scanning directions that can be used with the scan patterns of FIG. 13.
Figure 15:
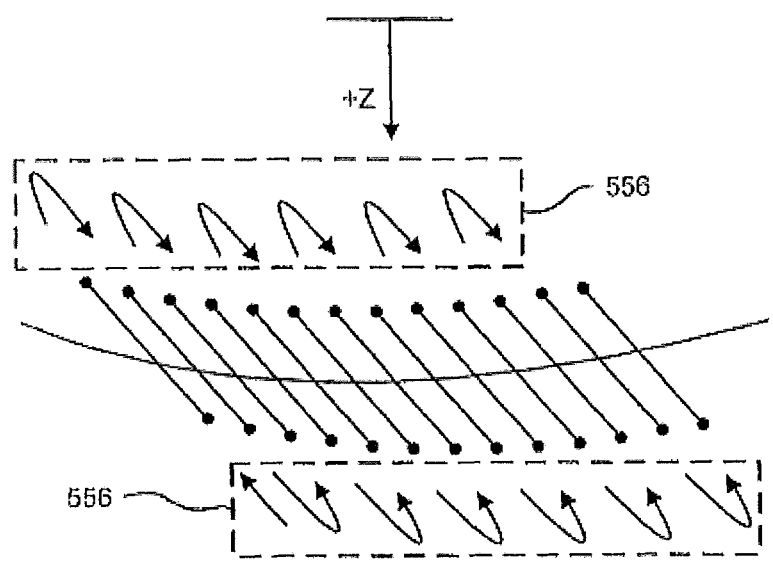

FIGS. 14 and 15 illustrate scanning directions 554, 556 that can be used to incise the series of scan patterns 550. While any suitable scanning directions can be used, the illustrated directions 554, 556 can be used to avoid having the electromagnetic radiation beam propagate through previously treated tissue/material prior to reaching the focal point.

In some embodiments, the capsulotomy scan may take longer than would be ideal due to the scan pattern being substantially longer in the z-depth dimension than the capsule to reduce the chances of incomplete cutting. For example, in some embodiments, the scan pattern may provide a 300 pm overlap to ensure incision through the lens capsule of the eye. Further, in some embodiments, laser spots may be smaller and thus may require more time to provide a continuous or nearly continuous incision. Accordingly some methods and systems may reduce the time for incising a capsulotomy by keeping the focus of an electromagnetic radiation beam on the capsular edge while incising so as to complete the incision using one or a few scans.

Figure 16:
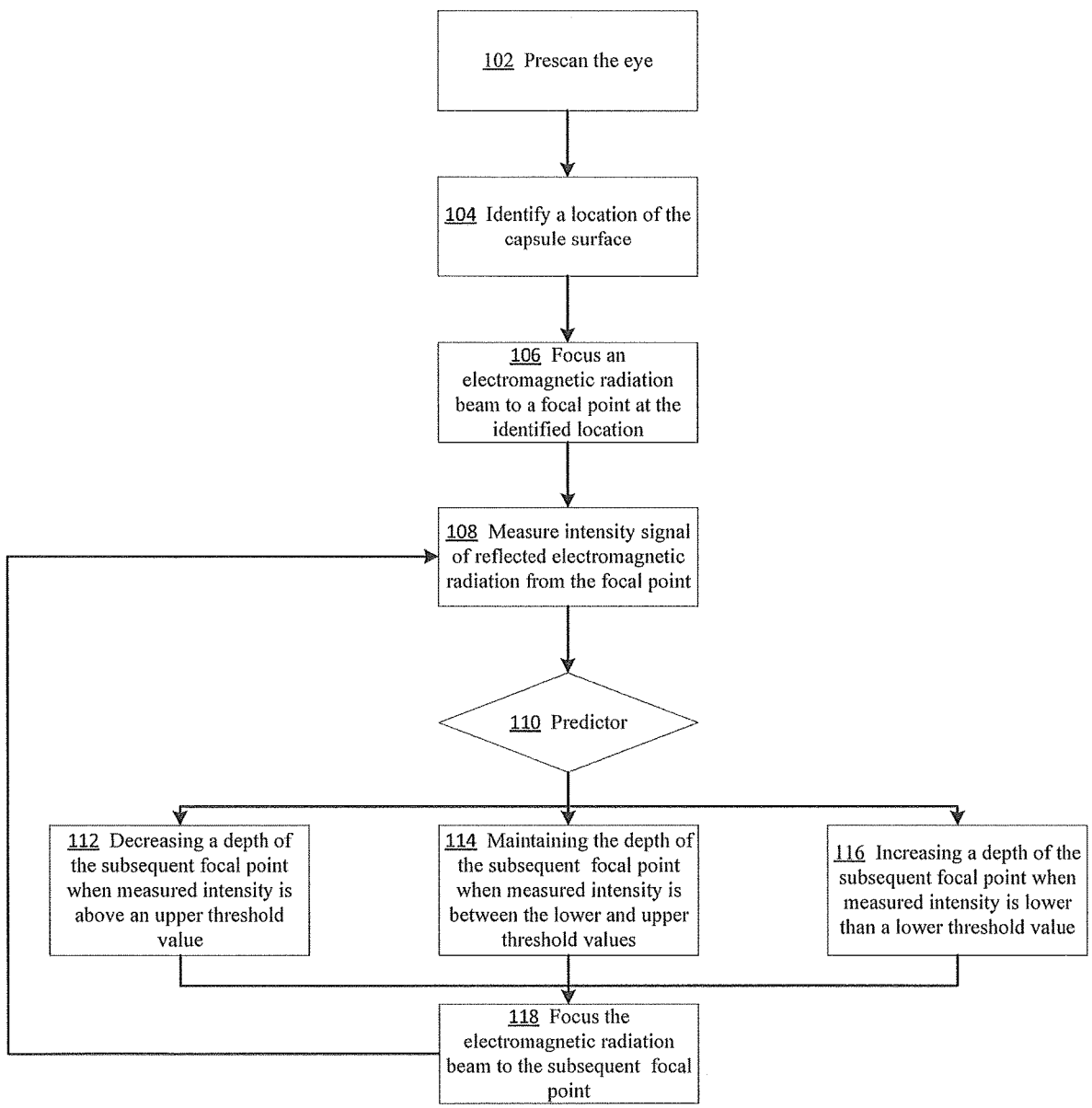
FIG. 16 is a simplified block diagrams of steps or acts of a method of imaging and adaptively modifying an intraocular target according to many embodiments.

FIG. 16 illustrates an exemplary method 100 of controlling the scanning of a focal point of an electromagnetic radiation beam to incise the lens capsule and reduce overlap. At step 102, an imaging prescan may be performed for aligning the focal point of an electromagnetic radiation beam. At step 104, a location of the capsule surface may be identified. At step 106, an electromagnetic radiation beam may be focused to a focal point at the identified location. At step 108, electromagnetic radiation may be reflected from the focal point in response to step 106. The reflected electromagnetic radiation may be measured 108 so as to generate a signal intensity. The measured signal intensity may be fed into a predictor algorithm block in software. The predictor block 110 identifies one of three conditions and issues an appropriate command. If the measured signal intensity is above an upper threshold value, predictor 110 may issue a command 112 to decrease a depth of the subsequent electromagnetic radiation focal point. If the measured signal intensity is below a lower threshold value, predictor 110 may issue a command 116 to increase a depth of the subsequent electromagnetic radiation focal point. If the measured signal intensity is above the lower threshold value and below the upper threshold value, the predictor 110 may issue command 114 to maintain a depth of the subsequent electromagnetic radiation focal point. Thereafter, method 100 proceeds to step 118 where the electromagnetic radiation beam is focused to the subsequent focal point. After step 118, the method 100 may loop back to step 108 where the signal intensity of reflected electromagnetic radiation from the focal point is measured. Step 108-118 may be repeated until the planned capsulotomy is completed.

While method 100 is described with regard to a capsulotomy incision, the method may be applicable incisions of other intraocular targets. In these instances, the other target tissues might be the corneal surfaces or intra-corneal reference surfaces like the corneal epithelium, Bowman's layer, intrastromal layers, or the endothelium.

Method 100 may be performed by the systems and devices described above. For example, steps 102 and 104 may be performed using confocal imaging. As mentioned above, imaging and cutting may be performed concurrently using the same electromagnetic radiation beam. Accordingly, such a system may be used to adjust the focal depth onto the capsule surface as a treatment beam incises the capsule. In some embodiments, the capsulotomy can be achieved with only one scan. In other embodiments, the incision is performed by two or more scans. This may be preferable to a 300 µm overlap since a capsulotomy may be performed much faster with one or a few scans thereby reducing the possibility of inadvertent eye/lens movement relative to the treatment system during or between scans. Further, with fewer scans of a treatment beam, the energy transmitted into the eye by scanning the focal point of an electromagnetic radiation beam may be reduced.

The pre-scan 102 may provide an estimated location of the lens prior to incising tissue in order to align the laser with the lens capsule. The focal point of an electromagnetic radiation beam can be scanned using a low imaging-only power level (e.g., a power level sufficient to provide for imaging of the intraocular target without modifying the intraocular target). It may be scanned along a projection of an intraocular incision designer such as capsulotomy incision designer 422. The depth of the focal point may be varied to determine a depth of the anterior lens capsule 104. The intensity of the reflected signal, however, rises from near zero to a peak value over a z-scan distance of about 30 µm as can be seen in FIG. 10; and the peak value may correspond to a depth of the anterior lens. Thus, locking onto the surface of the lens capsule may be somewhat challenging.

At step 106, a treatment beam (e.g., a beam with a power level sufficient to provide for target modification and/or incision) may be focused to a focal point at the identified anterior surface of the lens capsule. In some embodiments, a single treatment beam pulse is delivered to the location. Alternatively, a plurality of pulses (e.g., 100 pulses) may be fired at each depth prior to adjustment. This may be preferable in some instances where adjustment for each pulse may be challenging for the z-scan device. In some embodiments, the size of a single pulse may be 5 µm long and about 1 µm wide. Further, in some embodiments, it may not be necessary to cut completely through the capsule in order to sufficiently weaken the capsule for removal.

Since, the lens capsule can move slightly during surgery, step 108 and an estimator/predictor block 110 may be used to make corrections to the z-depth in near real time as the focal point of a treatment beam is scanned around the capsulotomy. These steps may help ensure correct positioning of the focal point relative to the capsular bag. At step 108, an intensity signal of reflected electromagnetic radiation from the focal point of the treatment beam is measured. Based on the intensity signal of the reflected electromagnetic radiation, the estimator/predictor block 110 may make adjustments to a focal point position when needed. As illustrated in FIG. 10, the peak intensity value may correspond to a focal point positioned posterior to the lens capsule. In contrast, the low intensity values may correspond to a focal point positioned anterior to the lens capsule or positioned in the aqueous humor of the eye. The lens capsule has an intensity value between the peak intensity value and the intensity value of focal points positioned in the aqueous humor of the eye. Accordingly, an intensity range having an upper threshold and a lower threshold may be defined for indicating a position of the lens capsule of the eye. A measured intensity signal of reflected electromagnetic radiation that is above the upper threshold value may suggest that the focal point of the treatment laser was located within the lens of the eye and posterior to the lens capsule. Thus, the depth of a subsequent focal point of the treatment beam should be decreased. A measured intensity signal of reflected electromagnetic radiation that is below the lower threshold value may suggest that the focal point of the treatment laser was located within the aqueous humor and anterior to the lens capsule. Thus, the depth of a subsequent focal point of the treatment beam should be increased. When the measured intensity signal of reflected electromagnetic radiation is above the lower threshold and below the upper threshold, it may suggest that the focal point of the treatment was located on or sufficiently near the lens capsule of the eye. Hence, the depth of a subsequent focal point of the treatment beam may be maintained.

Figure 17:
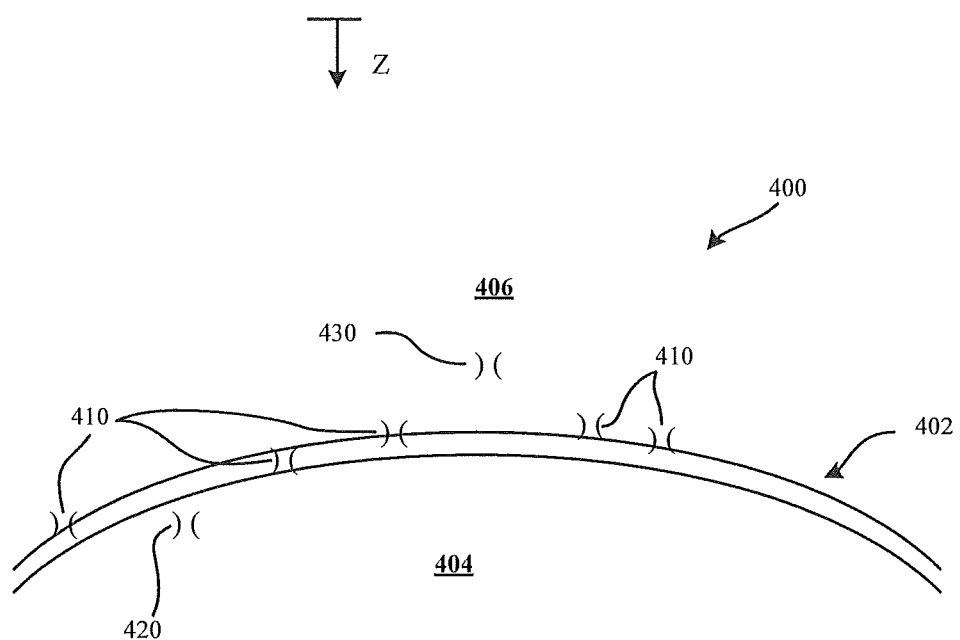
FIG. 17 illustrates a plurality of focus profiles located relative to a lens, a lens capsule, and the aqueous humor.

FIG. 17 illustrates exemplary focus profiles 400 located relative to a lens 402, lens capsule 404, and aqueous humor 406. In the illustrated figure, intensity signals of reflected electromagnetic radiation from focus profiles 410 may be between the lower and upper threshold values and thus indicate a focal point sufficiently close to the lens capsule 404. Accordingly, no depth adjustment may be necessary for subsequent focal points. The intensity signal of reflected electromagnetic radiation from focus profile 420 may be above the upper threshold value and thus indicates a focal point at too great a depth and within the lens 402. Accordingly, estimator/predictor 110 may decrease a depth of a subsequent focal point. Further, the intensity signal of reflected electromagnetic radiation from focus profile 430 may be below the lower threshold value and thus indicates a focal point at insufficient depth and within the aqueous humor 406. Accordingly, estimator/predictor 110 may increase a depth of a subsequent focal point.

As discussed above, in some embodiments, multiple pulses may be fired at a single depth prior to measuring and correcting a depth of subsequent pulses. In some embodiments, 2-200 pulses may be fired at a depth before measuring 108 and correcting with estimator/predictor 110, for example. Further, in some embodiments, a z-depth can be dithered to provide phase information of the intensity signal so as to indicate an a proper depth to place the incision at least partially inside the lens capsule. In such an embodiment, a z-depth may be dithered from a posterior position toward an anterior position to avoid transmitting the beam through modified tissue. Further, in some embodiments, at the start of an incision, a treatment beam may be started inward of the defined capsulotomy. The initial incision may bulge or otherwise deform the tissue such that the capsule can move out of alignment. Thus, in some embodiments, a treatment beam may be focused within the lens and a focal point depth may be decreased until the focal point is positioned on or substantially close to the lens capsule. Thereafter, the focal point may be scanned along the projection of the planned capsulotomy and the depth, may be adjusted according to the methods disclosed above.

Figure 18:
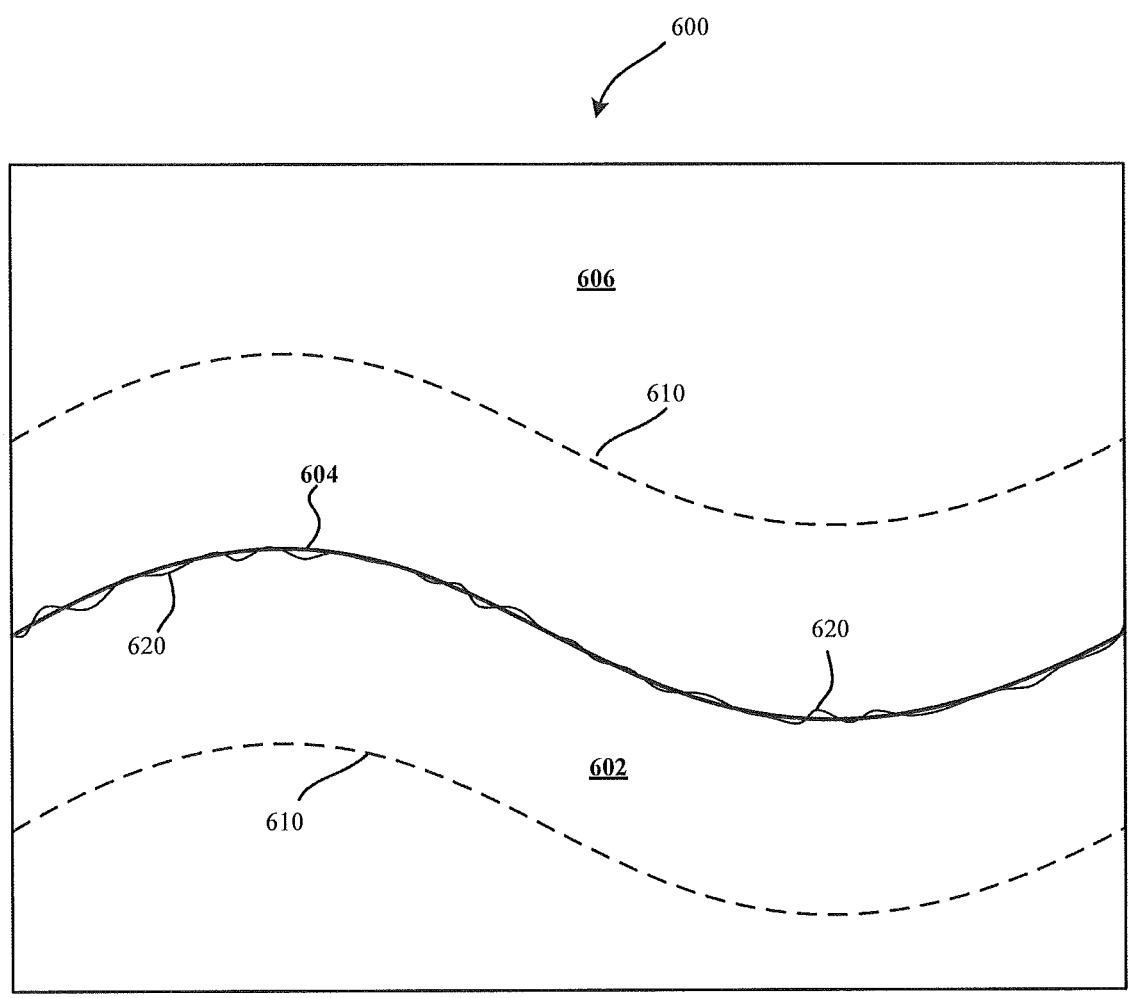
FIG. 18 illustrates an unwrapped scan of the eye including the lens, a lens capsule, and the aqueous humor, and an incision performed according to one or more methods disclosed herein.

FIG. 18 illustrates an exemplary scan 600 of the eye which is unwrapped. Scan 600 may include a lens 602, lens capsule 604, and aqueous humor 606. Lens capsule 604 may be approximately 8 µm thick. The dotted lines 610 illustrate a tolerance of 300 µm which may be used for some incisions. Such an incision may however, take more time due to the large overlap. Incision 620 may illustrate an incision performed by one of the above methods, such as method 100. In some embodiments, incision 620 may be performed with depth adjustments between each pulse. In other embodiments, incision 620 may be performed with depth adjustments between a plurality of pulses. In some embodiments, incision 620 may include pulses dithered in a z-direction. As can be appreciated, such a scan 620 may be performed with one or a few scans along a planned capsulotomy.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

While certain illustrated embodiments of this disclosure have been shown and described in an exemplary form with a certain degree of particularity, those skilled in the art will understand that the embodiments are provided by way of example only, and that various variations can be made without departing from the spirit or scope of the invention. Thus, it is intended that this disclosure cover all modifications, alternative constructions, changes, substitutions, variations, as well as the combinations and arrangements of parts, structures, and steps that come within the spirit and scope of the invention as generally expressed by the following claims and their equivalents.

What is claimed is:

1. A non-transitory computer readable storage medium comprising a set of computer executable instructions for modifying an intraocular target of an eye, wherein execution of the instructions by a computer processor causes the processor to carry out the steps of:
   controlling an electromagnetic beam source and optics to focus a treatment beam to a focal point at a first location in the eye to therapeutically alter tissue at the first location;
   controlling a detector to measure an intensity signal of electromagnetic radiation reflected from the focal point of the treatment beam at the first location;
   identifying a second location of the focal point, including determining a depth of the second location using a feedback loop based in part on the measured intensity signal of the electromagnetic radiation reflected from the focal point of the treatment beam at the first location;
   controlling the optics to move the focal point to the second location to therapeutically alter tissue at the second location; and
   repeating the step of controlling the detector to measure the intensity signal and the identifying step for the second location and a plurality of additional locations in the eye, and repeating the step of controlling the optics to scan the focal point for the plurality of additional locations, wherein the altering of the tissue at the first, second and the plurality of additional locations collectively form an incision surface in the eye.

2. The non-transitory computer readable storage medium of claim 1, wherein the intraocular target is a lens capsule of the eye, the lens capsule surrounding a lens of the eye, and wherein execution of the instructions by the computer processor causes the processor to further carry out the steps of:
   controlling the optics to scan a focal point of an imaging beam within the eye;
   controlling the detector to measure an intensity signal of electromagnetic radiation reflected from the focal point locations in response to the imaging beam so as to locate the lens capsule of the eye;
   controlling the optics to align the treatment beam with the lens capsule.

3. The non-transitory computer readable storage medium of claim 1, wherein a depth of the focal point of the treatment beam is dithered.

4. The non-transitory computer readable storage medium of claim 3, wherein the focal point is scanned from a posterior depth toward an anterior depth.

5. The non-transitory computer readable storage medium of claim 3, wherein the focal point of the treatment beam is scanned in the xy-direction transverse to a propagation direction of the treatment beam.

6. The non-transitory computer readable storage medium of claim 1, wherein the depth of the second location in the eye is determined based in part on phase information of the intensity signal.

7. The non-transitory computer readable storage medium of claim 1, wherein the depth of the second location is determined by comparing the measured intensity signal to an upper threshold value and a lower threshold value;
   wherein the depth of the identified second location is less than a depth of the first location when the measured intensity signal of the electromagnetic radiation reflected from the first location is above the upper threshold value;
   wherein the depth of the identified second location is greater than the depth of the first location when the measured intensity signal of the electromagnetic radiation reflected from the first location is below the lower threshold value; and
   wherein the depth of the identified second location is equal to the depth of the first location when the measured intensity signal of the electromagnetic radiation reflected from the first location is greater than the lower threshold value and less than the upper threshold value.

8. A system for modifying an intraocular target of an eye, the system comprising:
   an electromagnetic beam source configured to generate a treatment beam;
   optics configured to focus the treatment beam to a focal point and scan the focal point in the eye to therapeutically alter tissue;
   a detector configured to receive electromagnetic radiation reflected from the focal point of the treatment beam and to measure an intensity signal of the reflected electromagnetic radiation;

a controller coupled with the optics and the detector and configured to:
control the optics to scan the focal point at a first location in the eye to therapeutically alter tissue at the first location;
control the detector to measure the intensity signal of electromagnetic radiation reflected from the focal point of the treatment beam at the first location;
identify a second location of the focal point of the treatment beam, including determining a depth of the second location using a feedback loop based in part on the measured intensity signal of the electromagnetic radiation reflected from the focal point at the first location;
control the optics to move the focal point to the second location to therapeutically alter tissue at the second location; and
repeat the step of controlling the detector to measure the intensity signal and the identifying step for the second location and a plurality of additional locations in the eye, and repeat the step of controlling the optics to scan the focal point for the plurality of additional locations, wherein the altering of the tissue at the first, second and the plurality of additional locations collectively form an incision surface in the eye.

9. The system of claim 8, wherein the detector comprises a confocal detector.

10. The system of claim 8, wherein a depth of the focal point of the treatment beam is dithered by the controller.

11. The system of claim 10, wherein the controller control the optics to scan the focal point of the treatment beam from a posterior depth toward an anterior depth.

12. The system of claim 8, wherein the feedback loop is based in part on phase information of the measured intensity signal.

13. The system of claim 8, wherein the controller identifies the depth of the second location of the treatment beam focal point by comparing the measured intensity signal with an upper threshold value and a lower threshold value;
wherein the depth of the identified second location is less than a depth of the first location when the measured intensity signal of the electromagnetic radiation reflected from the first location is above the upper threshold value;
wherein the depth of the identified second location is greater than a depth of the first location when the measured intensity signal of the electromagnetic radiation reflected from the first location is below the lower threshold value; and
wherein the depth of the identified second location is equal to the depth of the first location when the measured intensity signal of the electromagnetic radiation reflected from the first location is greater than the lower threshold value and less than the upper threshold value.

14. The system of claim 8, wherein the electromagnetic beam source is further configured to generate an imaging beam, and wherein the optics are further configured to focus and scan the imaging beam to locations in the eye.

15. A system for modifying an intraocular target of an eye, the system comprising:
an electromagnetic beam source configured to generate a treatment beam;
optics configured to focus the treatment beam to a focal point and scan the focal point in the eye to therapeutically alter tissue;
a detector configured to receive electromagnetic radiation reflected from the treatment beam focal point and to measure an intensity signal of the reflected electromagnetic radiation;
a controller coupled with the optics and the detector and configured to:
control the optics to scan the focal point of the treatment beam in a plurality of scan patterns in the eye to therapeutically alter tissue at the focal point, the plurality of scan patterns collectively forming an incision surface in the eye that incises the intraocular target;
while scanning the focal point in each one of the plurality of scan patterns, control the detector to measure an intensity signal of electromagnetic radiation reflected by the tissue from the focal point during the scanning in that scan pattern; and
before scanning the focal point in each subsequent one of the plurality of scan patterns, configure the subsequent scan pattern at least in part based on the measured intensity signal that was measured while scanning the focal point during an immediately previous one of the plurality of scan patterns.

16. The system of claim 15, wherein the intraocular target is a lens capsule of the eye, the lens capsule surrounding a lens of the eye, wherein the electromagnetic beam source is further configured to generate an imaging beam, and wherein the controller is further configured to:
control the optics to scan a focal point of the imaging beam within the eye;
control an imaging device to measure an intensity signal of electromagnetic radiation reflected from focal point locations in response to the imaging beam so as to locate the lens capsule of the eye; and
align the treatment beam with the lens capsule.

17. The system of claim 15, wherein in each of the plurality of scan patterns, the focal point is scanned from a posterior depth toward an anterior depth.

18. The system of claim 15, wherein the plurality of scan patterns are spaced apart in a direction non-parallel to a direction of scan in each of the plurality of scan patterns.

19. The system of claim 15, wherein the configuring step comprises:
based on the measured intensity signal that was measured while scanning the focal point in the immediately previous scan pattern, determining a focal point location along the immediately previous scan pattern that corresponds to a highest peak of the measured intensity signal; and
determining a starting location and an ending location of the subsequent scan pattern at least in part based on the focal point location corresponding to the peak.

20. The system of claim 19, wherein the starting location is determined to be at a predetermined distance on one side of the focal point location corresponding to the peak and the ending location is determined to be at another predetermined distance on another side of the focal point location corresponding to the peak.

* * * * *